United States Patent
Lobb et al.

(10) Patent No.: US 11,207,339 B2
(45) Date of Patent: Dec. 28, 2021

(54) TARGETED CANCER THERAPY

(71) Applicants: The United States of America, as represented by the Secretary, Department of Health and Human Services, Bethesda, MD (US); Aleta Biotherapeutics, Inc., Natick, MA (US)

(72) Inventors: Roy Lobb, Westwood, MA (US); Paul David Rennert, Holliston, MA (US); John Todd Schiller, Kensington, MD (US)

(73) Assignees: The United States of America, as Represented by the Secretary, Department of Health and Human Services, Bethesda, MD (US); Aleta Biotherapeutics Inc., Natick, MA (US)

( * ) Notice: Subject to any disclaimer, the term of this patent is extended or adjusted under 35 U.S.C. 154(b) by 426 days.

(21) Appl. No.: 15/772,134

(22) PCT Filed: Oct. 28, 2016

(86) PCT No.: PCT/US2016/059452
§ 371 (c)(1),
(2) Date: Apr. 30, 2018

(87) PCT Pub. No.: WO2017/075440
PCT Pub. Date: May 4, 2017

(65) Prior Publication Data
US 2018/0311269 A1    Nov. 1, 2018

Related U.S. Application Data

(60) Provisional application No. 62/249,013, filed on Oct. 30, 2015.

(51) Int. Cl.
| | |
|---|---|
| *A61K 31/7088* | (2006.01) |
| *A61K 35/765* | (2015.01) |
| *A61K 39/00* | (2006.01) |
| *A61K 9/00* | (2006.01) |
| *A61K 35/761* | (2015.01) |
| *A61K 35/763* | (2015.01) |
| *A61K 35/766* | (2015.01) |
| *A61K 35/768* | (2015.01) |
| *C07K 14/705* | (2006.01) |

(52) U.S. Cl.
CPC ........ *A61K 31/7088* (2013.01); *A61K 9/0019* (2013.01); *A61K 35/761* (2013.01); *A61K 35/763* (2013.01); *A61K 35/765* (2013.01); *A61K 35/766* (2013.01); *A61K 35/768* (2013.01); *A61K 39/0011* (2013.01); *A61K 39/00115* (2018.08); *A61K 39/00116* (2018.08); *A61K 39/00117* (2018.08); *A61K 39/001104* (2018.08); *A61K 39/001106* (2018.08); *A61K 39/001109* (2018.08); *A61K 39/001112* (2018.08); *A61K 39/001113* (2018.08); *A61K 39/001119* (2018.08); *A61K 39/001122* (2018.08); *A61K 39/001124* (2018.08); *A61K 39/001166* (2018.08); *A61K 39/001168* (2018.08); *A61K 39/001171* (2018.08); *A61K 39/001174* (2018.08); *A61K 39/001182* (2018.08); *A61K 39/001186* (2018.08); *A61K 39/001188* (2018.08); *A61K 39/001191* (2018.08); *A61K 39/001192* (2018.08); *A61K 39/001195* (2018.08); *C07K 14/70503* (2013.01); *A61K 2039/5152* (2013.01); *A61K 2039/5156* (2013.01); *A61K 2039/5158* (2013.01); *Y02A 50/30* (2018.01)

(58) Field of Classification Search
CPC ................... A61K 39/0011; A61K 2039/5156
See application file for complete search history.

(56) References Cited

U.S. PATENT DOCUMENTS

| | | |
|---|---|---|
| 4,625,014 A | 11/1986 | Senter et al. |
| 4,659,839 A | 4/1987 | Nicolotti |
| 5,334,711 A | 8/1994 | Sproat |
| 5,667,764 A | 9/1997 | Kopia et al. |
| 5,716,824 A | 2/1998 | Beigelman |
| 6,022,522 A | 2/2000 | Sweet et al. |
| 6,180,389 B1 | 1/2001 | Douglas et al. |
| 6,416,945 B1 | 7/2002 | McCarthy et al. |
| 6,599,739 B1 | 7/2003 | Lowy et al. |
| 6,719,958 B1 | 4/2004 | Gozzini et al. |
| 6,984,386 B2 | 1/2006 | Douglas et al. |
| 6,991,795 B1 | 1/2006 | Lowe et al. |

(Continued)

FOREIGN PATENT DOCUMENTS

| | | |
|---|---|---|
| CN | 1904012 A | 1/2007 |
| EP | 1491210 A1 | 12/2004 |

(Continued)

OTHER PUBLICATIONS

Hajitou (Cell, 236:385-398, 2006).*
[No Author Listed] Bac-to-Bac Baculovirus Expression System. An efficient site-specific transposition system to generate baculovirus for high-level expression of recombinant proteins. Sep. 4, 2010. Retrieved from the Internet on Sep. 23, 2013. 80 pages.
[No Author Listed] GenBank Accession No. P03101, Major Capsid Protein L1, Jan. 11, 2011.

(Continued)

*Primary Examiner* — Valarie E Bertoglio
(74) *Attorney, Agent, or Firm* — Choate, Hall & Stewart LLP; Brenda Herschbach Jarrell; Rolando Medina

(57) ABSTRACT

Some embodiments of the present disclosure are directed to methods that include delivering to a subject a nucleic acid encoding an antigen, wherein the nucleic acid is delivered via a tumor-selective vehicle or via intratumoral injection, and delivering to the subject an immune cell expressing a receptor that binds to the antigen.

17 Claims, 6 Drawing Sheets
Specification includes a Sequence Listing.

(56) References Cited

U.S. PATENT DOCUMENTS

| | | |
|---|---|---|
| 7,205,126 B2 | 4/2007 | Qiao et al. |
| 7,351,533 B2 | 4/2008 | McCarthy et al. |
| 7,951,379 B2 | 5/2011 | Kuroda et al. |
| 8,394,411 B2 | 3/2013 | Roberts et al. |
| 9,700,639 B2 | 7/2017 | de los Pinos et al. |
| 9,724,404 B2 | 8/2017 | Coursaget et al. |
| 9,855,347 B2 | 1/2018 | de los Pinos et al. |
| 2003/0129583 A1 | 7/2003 | Martin et al. |
| 2003/0206887 A1 | 11/2003 | Morrissey et al. |
| 2004/0005338 A1 | 1/2004 | Bachmann et al. |
| 2004/0028694 A1 | 2/2004 | Young et al. |
| 2004/0115132 A1 | 6/2004 | Young et al. |
| 2004/0121465 A1 | 6/2004 | Robinson |
| 2004/0146531 A1 | 7/2004 | Antonsson et al. |
| 2004/0152181 A1 | 8/2004 | McCarthy et al. |
| 2005/0112141 A1 | 5/2005 | Terman |
| 2005/0118191 A1 | 6/2005 | Robinson et al. |
| 2005/0181064 A1 | 8/2005 | Kuroda |
| 2006/0088536 A1 | 4/2006 | Kuroda |
| 2006/0141042 A1 | 6/2006 | Kuroda |
| 2006/0166913 A1 | 7/2006 | Suzuki |
| 2006/0204444 A1 | 9/2006 | Young et al. |
| 2006/0216238 A1 | 9/2006 | Manchester et al. |
| 2006/0269954 A1 | 11/2006 | Lowy et al. |
| 2007/0059245 A1 | 3/2007 | Young et al. |
| 2007/0059746 A1 | 3/2007 | Kuroda |
| 2007/0258889 A1 | 11/2007 | Douglas et al. |
| 2009/0012022 A1 | 1/2009 | Milner et al. |
| 2009/0041671 A1 | 2/2009 | Young et al. |
| 2010/0135902 A1 | 6/2010 | Roberts et al. |
| 2011/0052496 A1 | 3/2011 | Cid-Arregui |
| 2011/0065173 A1 | 3/2011 | Kingsman et al. |
| 2011/0104051 A1 | 5/2011 | Francis et al. |
| 2012/0015899 A1 | 1/2012 | Lomonossoff et al. |
| 2012/0171290 A1 | 7/2012 | Coursaget et al. |
| 2012/0207840 A1 | 8/2012 | de los Pinos |
| 2013/0071414 A1 | 3/2013 | Dotti et al. |
| 2013/0115247 A1 | 5/2013 | de los Pinos et al. |
| 2013/0116408 A1 | 5/2013 | de los Pinos |
| 2013/0136689 A1 | 5/2013 | Rohlff et al. |
| 2014/0377170 A1 | 12/2014 | de los Pinos et al. |
| 2016/0228568 A1 | 8/2016 | de los Pinos et al. |
| 2017/0274099 A1 | 9/2017 | de los Pinos et al. |
| 2017/0368162 A1 | 12/2017 | Coursaget et al. |
| 2018/0110883 A1 | 4/2018 | de los Pinos et al. |

FOREIGN PATENT DOCUMENTS

| | | |
|---|---|---|
| JP | 2007-65646 A | 3/2007 |
| WO | 91/03162 A1 | 3/1991 |
| WO | 92/07065 A1 | 4/1992 |
| WO | 93/15187 A1 | 8/1993 |
| WO | 97/26270 A2 | 7/1997 |
| WO | 99/15630 A1 | 4/1999 |
| WO | 00/09673 A1 | 2/2000 |
| WO | WO-01/55393 A2 | 8/2001 |
| WO | 03/008573 A2 | 1/2003 |
| WO | 2005/051431 A1 | 6/2005 |
| WO | 2005/086667 A2 | 9/2005 |
| WO | 2006/125997 A1 | 11/2006 |
| WO | 2008/048288 A2 | 4/2008 |
| WO | 2008/054184 A1 | 5/2008 |
| WO | 2008/103920 A2 | 8/2008 |
| WO | 2008/140961 A2 | 11/2008 |
| WO | WO-2010/027827 A2 | 3/2010 |
| WO | 2010/120266 A1 | 10/2010 |
| WO | 2011/039646 A2 | 4/2011 |
| WO | 2013/080187 A1 | 6/2013 |
| WO | 2013/119877 A1 | 8/2013 |
| WO | 2014/039523 A1 | 3/2014 |
| WO | 2015/042325 A1 | 3/2015 |
| WO | WO-2015/075468 A1 | 5/2015 |
| WO | WO-2015/120363 A1 | 8/2015 |
| WO | WO-2015/142675 A2 | 9/2015 |
| WO | 2016/139362 A1 | 9/2016 |
| WO | WO-2017/075440 A1 | 5/2017 |

OTHER PUBLICATIONS

Alvarez, Insertion de sequences peptidiques dans la proteine majeure de capside du papillomavirus de type 16: application au ciblage pulmonaire de vecteurs derives et a la production d'un vaccine chimerique. Thesis. Universite Francois Rabelais. Jun. 20, 2006. 203 pages.

Bergsdorf et al., Highly efficient transport of carboxyfluorescein diacetate succinimidyl ester into COS7 cells using human papillomavirus-like particles. FEBS Lett. Feb. 11, 2003;536(1-3):120-4.

Bousarghin et al., Inhibition of cervical cancer cell growth by human papillomavirus virus-like particles packaged with human papillomavirus oncoprotein short hairpin RNAs. Mol Cancer Ther. Feb. 2009;8(2):357-65. Epub Jan. 27, 2009.

Brumfield et al., Heterologous expression of the modified coat protein of Cowpea chlorotic mottle bromovirus results in the assembly of protein cages with altered architectures and function. J Gen Virol. Apr. 2004;85(Pt 4): 1049-53.

Buck et al., Efficient intracellular assembly of papillomaviral vectors. J Virol. Jan. 2004;78(2):751-7.

Buck et al., Production of papillomavirus-based gene transfer vectors. Current Protocols in Cell Biology. 26.1.1-26.1.19, Dec. 2007.

Butz et al., siRNA targeting of the viral E6 oncogene efficiently kills human papillomavirus-positive cancer cells. Oncogene. Sep. 4, 2003;22(38):5938-45.

Carpentier et al. Mutations on the FG surface loop of human papillomavirus type 16 major capsid protein affect recognition by both type-specific neutralizing antibodies and cross-reactive antibodies. J Med Viral. Dec. 2005;77(4):558-65. Abstract only.

Carpentier et al., Cell targeting for CF gene therapy: Identification of a new specific cell ligand and selection of infectious papillomavirus mutants. J Cystic Fibro. Jun. 1, 2009;8:S31.

Carpentier, Retargeting human papillomavirus-mediated gene transfer to human airway epithelial cells. J Cystic Fibro. Jun. 1, 2010 ; 9:S17.

Carter et al., Identification of a human papillomavirus type 16-specific epitope on the C-terminal arm of the major capsid protein L1. J Virol. Nov. 2003;77(21):11625-32.

Carter et al., Identification of human papillomavirus type 16 L1 surface loops required for neutralization by human sera. J Virol. May 2006;80(10):4664-72.

Christensen et al. Surface conformational and linear epitopes on HPV-16 and HPV-18 L1 virus-like particles as defined by monoclonal antibodies. Virology. Sep. 1, 1996;223(1):174-84.

Cohen et al., Targeted in vitro photodynamic therapy via aptamer-labeled, porphyrin-loaded virus capsids. J Photochem Photobiol B. Apr. 5, 2013;121:67-74. doi: 10.1016/j.jphotobiol.2013.02.013. Epub Feb. 28, 2013.

Combita et al., Gene transfer using human papillomavirus pseudovirions varies according to virus genotype and requires cell surface heparan sulfate. FEMS Microbiol Lett. Oct. 16, 2001;204(1):183-8.

Cook et al., Purification of virus-like particles of recombinant human papillomavirus type 11 major capsid protein L1 from Saccharomyces cerevisiae. Protein Expr Purif. Dec. 1999;17(3):477-84.

Douglas et al., Protein engineering of a viral cage for constrained nanomaterials synthesis. Adv Mater. Mar. 12, 2002;14(6):415-8.

Elbashir et al., Analysis of gene function in somatic mammalian cells using small interfering RNAs. Methods. Feb. 2002;26(2):199-213.

Ewers et al., GM1 structure determines SV40-induced membrane invagination and infection. Nat Cell Biol. Jan. 2010;12(1):11-20; sup pp. 1-12. doi: 10.1038/ncb1999. Epub Dec. 20, 2009.

Finnen et al., Interactions between papillomavirus L1 and L2 capsid proteins. J Viral. Apr. 2003;77(8):4818-26.

Fleury et al., Identification of neutralizing conformational epitopes on the human papillomavirus type 31 major capsid protein and functional implications. Protein Sci. Jul. 2009;18(7):1425-38.

(56) References Cited

OTHER PUBLICATIONS

Gaden et al., Gene transduction and cell entry pathway of fiber-modified adenovirus type 5 vectors carrying novel endocytic peptide ligands selected on human tracheal glandular cells. J Virol. Jul. 2004;78(13):7227-47.
Gillitzer et al., Controlled ligand display on a symmetrical protein-cage architecture through mixed assembly. Small. Aug. 2006;2(8-9):962-6.
Hagensee et al. Self-assembly of human papillomavirus type 1 capsids by expression of the L1 protein alone or by coexpression of the L1 and L2 capsid proteins. Journal of virology. Jan. 1, 1993;67(1):315-22.
Jiang et al., Gel-based application of siRNA to human epithelial cancer cells induces RNAi-dependent apoptosis. Oligonucleotides. 2004 Winter;14(4):239-48.
Jiang et al., Selective silencing of viral gene E6 and E7 expression in HPV-positive human cervical carcinoma cells using small interfering RNAs. Methods Mol Biol. 2005;292:401-20.
Jiang et al., Selective silencing of viral gene expression in HPV-positive human cervical carcinoma cells treated with siRNA, a primer of RNA interference. Oncogene. Sep. 5, 2002;21(39):6041-8.
Jost et al., A novel peptide, THALWHT, for the targeting of human airway epithelia. FEBS Lett. Feb. 2, 2001;489(2-3):263-9.
Kawana et al., In vitro construction of pseudovirions of human papillomavirus type 16: incorporation of plasmid DNA into reassembled L1/L2 capsids. J Virol. Dec. 1998;72(12):10298-300.
Kines et al., Human papillomavirus capsids preferentially bind and infect tumor cells. Int J Cancer. Feb. 15, 2016;138(4):901-11. doi: 10.1002/ijc.29823. Epub Oct. 27, 2015.
Kirnbauer et al. Efficient self-assembly of human papillomavirus type 16 L1 and L1-L2 into virus-like particles. Journal of virology. Dec. 1, 1993;67(12):6929-36.
Kirnbauer et al. Papillomavirus L1 major capsid protein self-assembles into virus-like particles that are highly immunogenic. Proceedings of the National Academy of Sciences. Dec. 15, 1992;89(24):12180-4.
Lavelle et al., The disassembly, reassembly and stability of CCMV protein capsids. J Virol Methods. Dec. 2007;146(1-2):311-6. Epub Sep. 4, 2007.
Lee et al., Adaptations of nanoscale viruses and other protein cages for medical applications. Nanomedicine. Sep. 2006;2(3):137-49.
Leong et al., Intravital imaging of embryonic and tumor neovasculature using viral nanoparticles. Nat Protoc. Aug. 2010;5(8):1406-17. doi: 10.1038/nprot.2010.103. Epub Jul. 8, 2010.
Li et al., Expression of the human papillomavirus type 11 L1 capsid protein in *Escherichia coli*: characterization of protein domains involved in DNA binding and capsid assembly. J Viral. Apr. 1997;71(4):2988-95.
Li et al., Trackable and Targeted Phage as Positron Emission Tomography (PET) Agent for Cancer Imaging. Theranostics. 2011;1:371-80. Epub Nov. 18, 2011.
Mitsunaga et al., In vivo longitudinal imaging of experimental human papillomavirus infection in mice with a multicolor fluorescence mini-endoscopy system. Cancer Prev Res (Phila). May 2011;4(5):767-73. doi: 10.1158/1940-6207.CAPR-10-0334. Epub Mar. 23, 2011.
Oh et al., Enhanced mucosal and systemic immunogenicity of human papillomavirus-like particles encapsidating interleukin-2 gene adjuvant. Virology. Oct. 25, 2004;328(2):266-73.
Pedersen et al. Immunization of early adolescent females with human papillomavirus type 16 and 18 L1 virus-like particle vaccine containing AS04 adjuvant. Journal of Adolescent Health. Jun. 30, 2007;40(6):564-71.
Pinto et al. Cellular immune responses to human papillomavirus (HPV)-16 L1 in healthy volunteers immunized with recombinant HPV-16 L1 virus-like particles. Journal of Infectious Diseases. Jul. 15, 2003;188(2):327-38.

Pyeon et al., Production of infectious human papillomavirus independently of viral replication and epithelial cell differentiation. Proc Natl Acad Sci U S A. Jun. 28, 2005;102(26):9311-6. Epub Jun. 15, 2005.
Raja et al., Hybrid virus-polymer materials. 1. Synthesis and properties of PEG-decorated cowpea mosaic virus. Biomacromolecules. May-Jun. 2003;4(3):472-6.
Rose et al. Expression of human papillomavirus type 11 L1 protein in insect cells: in vivo and in vitro assembly of viruslike particles. Journal of Virology. Apr. 1, 1993;67(4):1936-44.
Rudolf et al., Human dendritic cells are activated by chimeric human papillomavirus type-16 virus-like particles and induce epitope-specific human T cell responses in vitro. J Immunol. May 15, 2001;166(10):5917-24.
Ryding et al., Deletion of a major neutralizing epitope of human papillomavirus type 16 virus-like particles. J Gen Virol. Mar. 2007;88(Pt 3):792-802.
Sadeyen et al., Insertion of a foreign sequence on capsid surface loops of human papillomavirus type 16 virus-like particles reduces their capacity to induce neutralizing antibodies and delineates a conformational neutralizing epitope. Virology. Apr. 25, 2003;309(1):32-40.
Schädlich et al., Refining HPV 16 L1 purification from *E. coli*: reducing endotoxin contaminations and their impact on immunogenicity. Vaccine. Mar. 4, 2009;27(10):1511-22. Epub Jan. 25, 2009.
Singh, Tumor targeting using canine parvovirus nanoparticles. Curr Top Microbiol Immunol. 2009;327:123-41.
Speir et al., Structures of the native and swollen forms of cowpea chlorotic mottle virus determined by X-ray crystallography and cryo-electron microscopy. Structure. Jan. 15, 1995;3(1):63-78.
Stephanopoulos et al., Dual-surface modified virus capsids for targeted delivery of photodynamic agents to cancer cells. ACS Nano. Oct. 26, 2010;4(10):6014-20. doi: 10.1021/nn1014769.
Touze et al., In vitro gene transfer using human papillomavirus-like particles. Nucleic Acids Res. Mar. 1, 1998;26(5):1317-23.
Touze et al., The L1 major capsid protein of human papillomavirus type 16 variants affects yield of virus-like particles produced in an insect cell expression system. J Clin Microbiol. Jul. 1998;36(7):2046-51.
Touzé et al., The nine C-terminal amino acids of the major capsid protein of the human papillomavirus type 16 are essential for DNA binding and gene transfer capacity. FEMS Microbiol Lett. Aug. 1, 2000; 189(1):121-7.
Uchida et al., Biological Containers: Protein Cages as Multifunctional Nanoplatforms. Adv Mater. 2007;19:1025-42.
Varsani et al., Chimeric human papillomavirus type 16 (HPV-16) L1 particles presenting the common neutralizing epitope for the L2 minor capsid protein of HPV-6 and HPV-16. J Virol. Aug. 2003;77(15):8386-93.
Vaysse et al., Improved transfection using epithelial cell line-selected ligands and fusogenic peptides. Biochim Biophys Acta. Jul. 26, 2000;1475(3):369-76.
Wang et al., Insertion of a targeting peptide on capsid surface loops of human papillomavirus type-16 virus-like particles mediate elimination of anti-dsDNA Abs-producing B cells with high efficiency. J Immunother. Jan. 2009;32(1):36-41.
Wang et al., Expression of Human Papillomavirus Type 6 L1 and L2 Isolated in China and Self Assembly of Virus-like Particles by the Products. Acta Biochimica et Biophysica Sinica. 2003;35(1):27-34. 10 pages.
Wang et al., Human papillomavirus type 6 virus-like particles present overlapping yet distinct conformational epitopes. J Gen Virol. Jun. 2003;84(Pt 6):1493-7.
White et al., Genetic modification of adeno-associated viral vector type 2 capsid enhances gene transfer efficiency in polarized human airway epithelial cells. Hum Gene Ther. Dec. 2008;19(12):1407-14.
Willits et al., Effects of the cowpea chlorotic mottle bromo virus beta-hexamer structure on virion assembly. Virology. Feb. 15, 2003;306(2):280-8.
Xu et al., Papillomavirus virus-like particles as vehicles for the delivery of epitopes or genes. Arch Virol. Nov. 2006;151(11):2133-48. Epub Jun. 22, 2006.

(56) References Cited

OTHER PUBLICATIONS

Yoshinouchi et al., In vitro and in vivo growth suppression of human papillomavirus 16-positive cervical cancer cells by E6 siRNA. Mol Ther. Nov. 2003;8(5):762-8.

Zhang et al. Expression of Human Papillomavirus Type 16 L1 Protein in *Escherichia coli*: Denaturation, Renaturation, and Self-Assembly of Virus-like Particlesin Vitro. Virology. Apr. 10, 1998;243(2):423-31.

Zhou et al. Expression of vaccinia recombinant HPV 16 L1 and L2 ORF proteins in epithelial cells is sufficient for assembly of HPV virion-like particles. Virology. Nov. 1, 1991;185(1):251-7.

U.S. Appl. No. 13/264,213, filed Mar. 2, 2012, Granted, U.S. Pat. No. 9,724,404.

U.S. Appl. No. 15/636,112, filed Jun. 28, 2017, Published, 2017-0368162.

U.S. Appl. No. 14/376,408, filed Aug. 1, 2014, Granted, U.S. Pat. No. 9,700,639.

U.S. Appl. No. 15/615,485, filed Jun. 6, 2017, Granted, U.S. Pat. No. 9,855,347.

U.S. Appl. No. 15/824,685, filed Nov. 28, 2017, Pending, 2018-0110883.

U.S. Appl. No. 15/023,169, filed Mar. 18, 2016, Published, 2016-0228568.

U.S. Appl. No. 15/772,152, filed Apr. 30, 2018, Pending.

PCT/IB2010/002654, Aug. 18, 2011, International Search Report and Written Opinion.

PCT/US2016/059452, Jan. 30, 2017, Invitation to Pay Additional Fees.

PCT/US2016/059452, April 10, 2017, International Search Report and Written Opinion.

PCT/US2016/059452, May 11, 2018, International Preliminary Report on Patentability.

International Search Report for PCT/US16/59452, 6 pages (Apr. 10, 2017).

Ruehlmann, J. et al., MIG (CXCL9) chemokine gene therapy combines with antibody-cytokine fusion protein to suppress growth and dissemination of murine colon carcinoma, Cancer Res., 61(23):8498-8503 (2001).

Written Opinion for PCT/US16/59452, 12 pages (dated Apr. 10, 2017).

\* cited by examiner

SEQUENCE LISTING

```
<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 1
agctgtatgt gtgggc                                                     16

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
gctccacact ttggctgt                                                   18

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
cttcaaagtg acgcctcc                                                   18

<210> SEQ ID NO 4
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 4
tctatgagaa cgactcc                                                    17
```

TARGETED CANCER THERAPY

RELATED APPLICATIONS

This application is a national stage filing under 35 U.S.C. § 371 of international application number PCT/US2016/059452, filed Oct. 28, 2016, which was published under PCT Article 21(2) in English and claims the benefit under 35 U.S.C. § 119(e) of U.S. provisional application No. 62/249,013, filed Oct. 30, 2015, each of which is incorporated by reference herein in its entirety.

BACKGROUND

Adoptive cell transfer is a targeted immune cell therapy that often involves engineering a patient's immune cells to recognize and attack his or her tumor(s). Immune cells collected from a patient's blood can be genetically engineered to express receptors on the immune cell surface, which permits recognition by the immune cells of specific ligand proteins (antigens) expressed on a tumor cell surface. In vitro-expanded populations of these genetically-engineered immune cells are infused back into the patient, the immune cells multiply in the patient's body and, with guidance from the engineered receptors, recognize and kill cancer cells that harbor the surface antigen.

SUMMARY

One approach to immunotherapy involves engineering a patient's own immune cells to recognize and attack his or her tumors. Often, however, the engineered immune cells attack normal cells as well as tumor cells, thus lowering the efficacy of the immunotherapy and increasing unwanted side-effects. This is in part because the tumor cells and the normal cells can express similar surface antigens at different levels. The present disclosure provides compositions and methods for selectively targeting immune cells to tumor cells for the treatment of cancer. This selectively results from engineering (e.g., genetically engineering) tumor cells and immune cells of a subject in a complementary fashion resulting in a highly specific immunotherapeutic targeting system. In some embodiments, the tumor cells are engineered to express antigens (e.g., non-self antigens) that are not expressed by normal (non-tumor) cells, while in other embodiments, the tumor cells are engineered to express antigens (e.g., self-antigens) at an expression level higher than the expression level at which a normal tumor cell expresses the same antigen. These antigens are then selectively bound by immune cells engineered to express cognate receptors (receptors that bind specifically to those antigens). In some embodiments, tumor cells are engineered to express antigens (e.g., self antigens) at a level similar to the level expressed on normal cells. These normal cells (e.g., B cells) are typically deleted along with the tumor cells, although this causes little or no toxicity in the patient.

Thus, embodiments of the present disclosure provide methods that include delivering to a subject an (at least one) engineered nucleic acid encoding an (at least one) antigen, wherein the engineered nucleic acid is delivered via a tumor-selective vehicle or via intratumoral injection, and delivering to the subject an immune cell (e.g., leukocyte) expressing a receptor that binds to the antigen. In some embodiments, at least two (e.g., at least 3, at least 4, at least 5) engineered nucleic acids, each encoding a different antigen, are delivered to a subject.

In some embodiments, an antigen is a self-antigen, a non-self antigen or a combination (recombinant chimera) of a self-antigen and a non-self antigen. A non-self antigen may be, for example, a bacterial, yeast, protozoan, viral, plant or fish antigen. In some embodiments, a non-self antigen is a synthetic (artificial) antigen.

In some embodiments, an antigen is a tumor antigen, such as a tumor-specific antigen (TSA) or a tumor-associated antigen (TAA). A tumor antigen may be or may comprise, for example, an epitope of CD19, CD20, CD21, CD22, CD45, BCMA, MART-1, MAGE-A3, glycoprotein 100 (gp100), NY-ESO-1, HER2 (ErbB2), IGF2B3, EGFRvIII, Kallikrein 4, KIF20A, Lengsin, Meloe, MUC-1, MUCSAC, MUC-16, B7-H3, B7-H6, CD70, CEA, CSPG4, EphA2, EpCAM, EGFR family, FAP, FRα, glupican-3, GD2, GD3, HLA-A1+MAGE1, IL-11Rα, IL-23Rα2, Lewis-Y, mesothelin, NKG2D ligands, PSMA, ROR1, survivin, TAG72 or VEGFR2.

In some embodiments, an engineered nucleic acid encoding the antigen is encapsulated within the tumor-selective vehicle.

In some embodiments, a tumor-selective vehicle is a virus (e.g., naturally-occurring, modified or hybrid virus), a virus-like particle or a pseudovirus. In some embodiments, a virus is an oncolytic virus, such as an adenovirus, a vaccinia virus, a Sindbis virus, a Seneca valley virus, a Coxsackie virus, a measles virus, a reovirus, a vaccinia virus, a Newcastle disease virus, a vesicular stomatitis virus, a herpes simplex virus, a poliovirus, or a parvovirus.

In some embodiments, a tumor-selective vehicle is a non-oncolytic virus that is modified to target tumor cells, such as an adeno-associated virus (AAV) that is modified to target tumor cells. In some embodiments, a tumor-selective vehicle is a chimeric virus between an eukaryotic and a prokaryotic virus, such as an adeno-associated virus (AAV) and a bacteriophage. For example, a chimeric virus may include elements (e.g., cis-elements) obtained from AAV and bacteriophage (phage). In some embodiments, the bacteriophage displays tumor targeting peptides.

In some embodiments, a tumor-selective vehicle is a papillomavirus or a papilloma pseudovirus. A papillomavirus may be a human papillomavirus, a modified human papillomavirus, or a non-human papillomavirus, such as a bovine papillomavirus.

In some embodiments, a tumor-selective vehicle is or comprises a natural polymer, a synthetic polymer, a cationic peptide, a cell-penetrating peptide, a biodegradable nanoparticle, a liposome, a lipoplex, a polyplex, a micelle, a dendrimer, a gel, a mucoadhesive or a silicon nanoneedle.

In some embodiments, a tumor-selective vehicle comprises a tumor-targeting agent (e.g., an alkylphosphocholine (APC) molecule). In some embodiments, a tumor targeting agent is a small molecule (drug or other chemical) or a peptide).

In some embodiments, an engineered nucleic acid encoding an antigen is a deoxyribonucleic acid (DNA) or a ribonucleic acid (RNA), such as a messenger RNA (mRNA).

In some embodiments, an immune cell is a leukocyte. A leukocyte, in some embodiments, is a neutrophil, an eosinophil, a basophil, a lymphocyte or a monocyte. In some embodiments, a leukocyte is a lymphocyte. A lymphocyte may be, for example, a T cell, a B cell, an NK cell, or an NKT cell. In some embodiments, an immune cell is a dendritic cell.

In some embodiments, a receptor expressed by an immune cell is a recombinant antigen receptor. In some embodiments, a receptor expressed by an immune cell (e.g., a T cell) is a chimeric antigen receptor.

In some embodiments, a tumor-selective vehicle is delivered via a parenteral, enteric or topical route. For example, a tumor-selective vehicle may be delivered via an intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (bolus or drip), intraventricular, intravesical or subcutaneous route.

In some embodiments, an engineered nucleic acid encoding an antigen is injected into the tumor.

Also provided herein are methods comprising delivering to a tumor an engineered nucleic acid that encodes an antigen (e.g. a non-self antigen), or delivering to a tumor an engineered nucleic acid that induces expression of a self-antigen, and delivering to the tumor an immune cell expressing a bispecific antigen receptor that binds two antigens. In some embodiments, the bispecific antigen receptor is a bispecific T cell receptor or a bispecific chimeric antigen receptor. In some embodiments, the bispecific antigen receptor binds to an antigen encoded by an engineered nucleic acid and binds to a self-antigen naturally expressed by the tumor. In some embodiments, the bispecific antigen binds to an antigen encoded by an engineered nucleic acid and binds to a non-tumor antigen present on a monocyte and provides an inhibitory signal.

Further provided herein are methods comprising delivering to a tumor two engineered nucleic acids that encode two different antigens, or delivering to a tumor two engineered nucleic acids that induce expression of two different self-antigens, and delivering to the tumor an immune cell expressing two different antigen receptors that respectively bind to each of the two different antigens. In some embodiments, the two different antigen receptors are recombinant T cell receptors or chimeric antigen receptors.

Also provided herein are methods comprising delivering to a tumor an engineered nucleic acids that encode an antigen, or delivering to a tumor an engineered nucleic acids that induce expression of a self-antigen, and delivering to the tumor an immune cell expressing two different antigen receptors, one of which binds to the antigen encoded by the engineered nucleic acid and the other of which binds to an antigen endogenously-expressed in the tumor. In some embodiments, the two different antigen receptors are recombinant T cell receptors or chimeric antigen receptors.

In some embodiments, a nucleic acid that induces expression of a self-antigen is a regulatory RNA or encodes a regulatory protein.

In some embodiments, an engineered nucleic acid that induces expression of a self-antigen contains a promoter (e.g., a natural promoter or a recombinant promoter). A promoter may be, for example, constitutive (e.g., CMV promoter) or inducible. In some embodiments, a promoter is a tissue-specific promoter.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 3A (left image) is an electrophoretic gel image showing purification fractions obtained from cell lysates of 293TT cells transfected with two DNA expression vectors: BPV1 L1/L2 and (human) hCD19 (clone #B, see FIG. 2) or (mouse) mCD19 (clone #6, see FIG. 2). The purest fractions are denoted by '*' and these were used in downstream validation experiments.

FIG. 4A. shows hCD19 surface expression in human cells of different lineages or cancer types. FIG. 4B shows mCD19 surface expression in murine TC-1 cells. For both FIG. 4A and FIG. 4B, surface staining for CD19 was completed 48 hours following infection with 1 µl of either modified HPV16/13 PsV or BPV PsV. GFP is also expressed on each CD19 expression vector and detection of its expression serves as an internal positive control for gene delivery.

DETAILED DESCRIPTION

Figure 1:
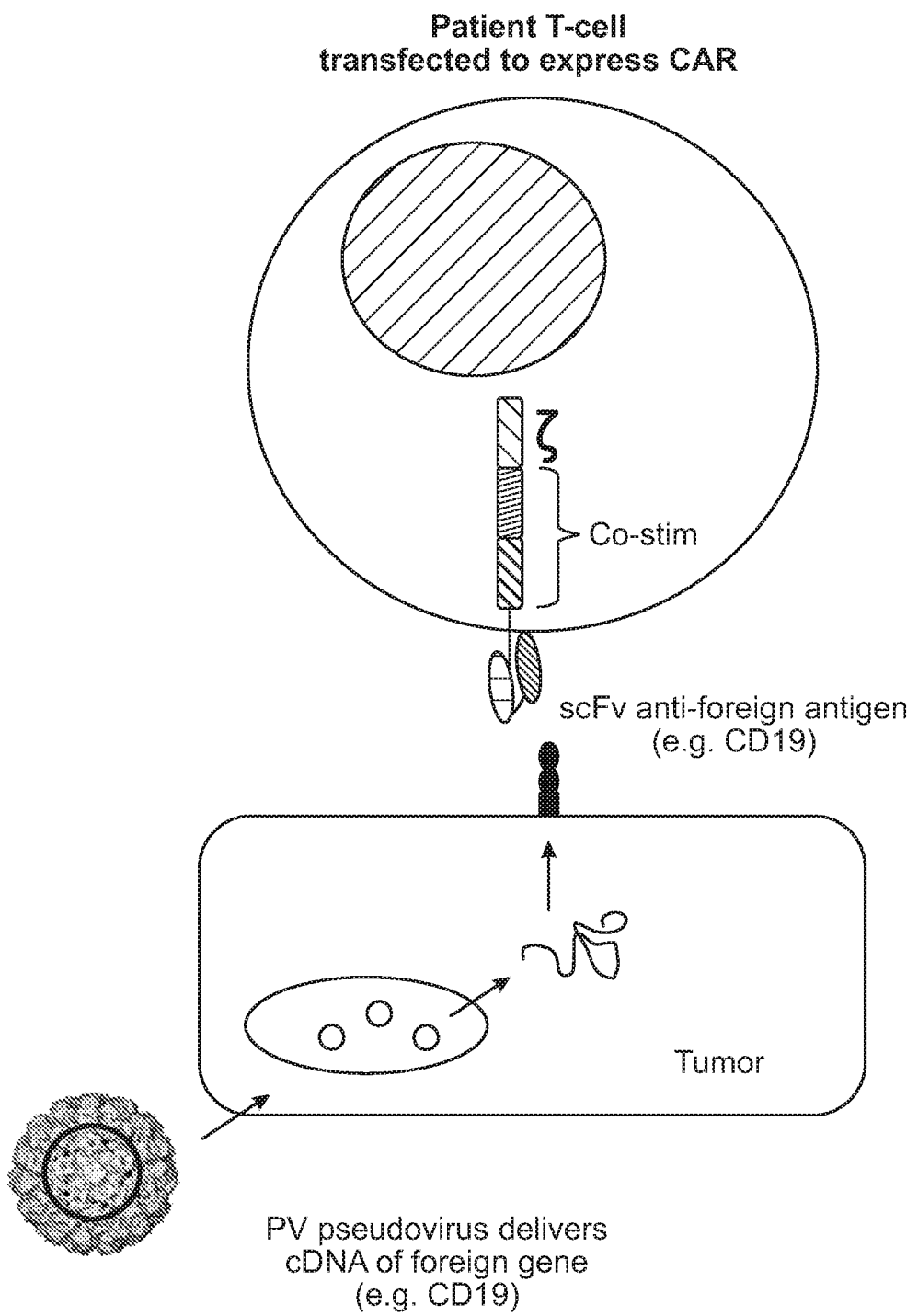
FIG. 1 depicts an example of a targeted cancer therapy of the present disclosure. In this example, a tumor-tropic papillomavirus (PV) pseudovirus (PsV) is engineered to encapsulate a nucleic acid encoding a CD19 antigen, and an immune cell (e.g., a T cell) is engineered to express a chimeric antigen receptor (CAR) that comprises a single chain antibody fragment (scFv) that binds specifically to a CD19 antigen. Both the PsV and the immune cell are administered to a subject having a tumor/tumor cells. The PsV serves as a vehicle to deliver the nucleic acid to the tumor cell(s), and the immune cell targets the tumor cell(s) following expression of CD19 at the cell surface.

Tumor cells typically express tumor antigens that trigger an immune response in a host subject. These tumor antigens serve as markers for identifying tumor cells and also serve as candidates for targeted cancer therapies. In many instances, however, the antigens expressed by a tumor are also expressed by some normal cells. These antigens are referred to as tumor-associated antigens. Thus, therapies designed to use tumor-associated antigens as signals to guide therapeutics to tumors risk also targeting normal cells, which can result in unwanted side-effects and lower therapeutic efficacy.

Provided herein are therapies used to selectively target tumor cells without also targeting a substantial number of normal cells, thereby reducing or eliminating unwanted side-effects and increasing efficacy of treatment. In some embodiments, immune cells and tumor cells of a subject are genetically engineered to express a receptor and cognate antigen, respectively. Modification of tumor cells in vivo, in some embodiments, is achieved by delivering to a subject a tumor-selective vehicle (that selectively homes to tumor cells) containing an engineered nucleic acid (or more than one engineered nucleic acid) that encodes an antigen (or encodes more than one antigen). In other embodiments, an engineered nucleic acid encoding an antigen is delivered directed to a tumor in vivo via intratumoral injection. Following delivery of the nucleic acid (or preceding or in combination with delivery of an engineered nucleic acid), immune cells engineered to express a cognate receptor (or receptors) are delivered to the subject. The immune cells, guided by receptor-antigen (ligand) binding, selectively target tumor cells expressing the antigen encoded by the engineered nucleic acid. The engineered immune cells then kill the tumor cells.

Antigens

Some embodiments of the present disclosure are directed to antigens, typically encoded by an engineered (exogenous) nucleic acid delivered via a tumor-selective vehicle or intratumoral injection. An "antigen" is a molecule that serves as a ligand for receptors of immune cells, including leukocytes, such as T cells. An antigen may be a self-antigen or a non-self antigen.

A "self-antigen" refers to an antigen that originates from within a body. Self-antigens may be expressed by tumor cells as well as some normal cells. In some embodiments, tumor cells express self-antigens at an expression level higher than the expression level at which a normal tumor cell expresses the same self-antigen. That is, the self-antigen expressed by a tumor cell is overexpressed. In some embodiments, an engineered nucleic acid encoding a self-antigen is delivered to tumor cells (via a tumor-selective vehicle or intratumoral injection) that naturally express, or overexpress, the self-antigen for the purpose of further increasing the expression level of the self-antigen. Thus, immune cells genetically engineered to express the cognate receptor selectively target the tumor cells over the normal cells. It should be understood that while "self-antigens" originate from within the body, a recombinant form of that antigen is still referred to as "self-antigen" if it is expressed in a tumor by an engineered (exogenously delivered) nucleic acid. For example, CD19 and CD20 are self-antigens overexpressed by tumor cells. The present disclosure encompasses delivering to a subject an engineered nucleic acid encoding CD19 or CD20—a step referred to herein as delivering to a subject an engineered nucleic acid encoding a self-antigen.

In some embodiments, an engineered nucleic acid encoding a self-antigen is delivered to tumor cells and is expressed at a level higher than the level at which the endogenous self-antigen is expressed in non-modified tumor cells (a tumor cell that does not contain an engineered nucleic acid). For example, a self-antigen encoded by an engineered nucleic acid operably linked to a strong constitutive promoter, such as the CMV promoter (e.g., CMV IE promoter) or the Grp78 promoter, may be expressed in tumor cells at a level that is 10%, 20%, 30%, 40%, 50%, 60%, 70%, 80%, 90%, 100%, 125%, 150%, 175% or 200% higher than the level at which the endogenous self-antigen is expressed in non-modified tumor cells.

In some embodiments, a self-antigen is a tumor antigen. A "tumor antigen" is an antigen expressed by tumor cells. Examples of tumor antigens of the present disclosure include, without limitation, CD19, CD20, CD21, CD22, CD45, BCMA, MART-1, MAGE-A3, glycoprotein 100 (gp100), NY-ESO-1, HER2 (ErbB2), IGF2B3, EGFRvIII, Kallikrein 4, KIF20A, Lengsin, Meloe, MUC-1, MUCSAC, MUC-16, B7-H3, B7-H6, CD70, CEA, CSPG4, EphA2, EpCAM, EGFR family, FAP, FRα, glupican-3, GD2, GD3, HLA-A1+MAGE1, IL-11Rα, IL-23Rα2, Lewis-Y, mesothelin, NKG2D ligands, PSMA, ROR1, survivin, TAG72 or VEGFR2. Other examples of tumor antigens are described (der Bruggen P et al. Peptide database: T cell-defined tumor antigens. *Cancer Immun* 2013. URL: cancerimmunity.org/peptide, incorporated herein by reference).

Tumor antigens include tumor-specific antigens (TSA) and tumor-associated antigens (TAA). "Tumor-specific antigens" are expressed only by tumor cells (not expressed on any other cell). "Tumor-associated antigens" are expressed by tumor cells and by some normal (non-tumor) cells.

Examples of tumor antigens include, without limitation, alpha-actinin-4, ARTC1, BCR-ABL, B-RAF, CASP-5, CASP-8, beta-catenin, Cdc27, CDK4, CDK12, CDKN2A, CLPP, COA-1, CSNK1A1, dek-can, EFTUD2, Elongation factor 2, ETV6-AML1, FLT3-ITD, FN1, GAS7, GPNMB, HAUS3, LDLR-fucosyltransferaseAS, HLA-A2, HLA-A11, hsp70-2, MART2, MATN, ME1, MUM-1, MUM-2, MUM-3, neo-PAP, Myosin class I, NFYC, OGT, OS-9, p53, pmI-RARalpha, PPP1R3B, PRDX5, PTPRK, K-ras, N-ras, RBAF600, SIRT2, SNRPD1, SYT-SSX1, SYT-SSX2, TGF-betaRII, Triosephosphate isomerase, BAGE family antigens, CAGE family antigens, Cyclin-A1, GAGE family antigens, HERV-K-MEL, KK-LC-1, KM-HN-1, LAGE-1, MAGE family antigens, NA88-A, NY-ESO-1/LAGE-2, PRAME, SAGE family antigens, Sp17, SSX family antigens, TAG-1, TAG-2, TRAG-3, TRP2-INT2, XAGE family antigens, CEA, Gp100/pmel17, mammaglobin-A, Melan-A/MART-1, mesothelin, NY-BR-1, OA1, PAP, PSA, RAB38/NY-MEL-1, TRP-1/gp75, TRP-2, tyrosinase, 9D7, adipophilin, AIM-2, ALDH1A1, BCLX (L), BING-4, CALCA, CD45, CD274, CPSF, cyclin-B1, cyclin D1, DKK1, ENAH (hMena), EpCAM, EphA3, EZH2, FGF5, Ganglioside GD3, glypican-3, G250/MN/CAIX, HER-2/neu, HLA-DOB, Hepsin, ISO1, IGF2B3, IL13Ralpha2, Intestinal carboxyl esterase, alpha-foetoprotein, Kallikrein 4, KIF20A, Lengsin, M-CSF, MCSP, mdm-2, Meloe, Midkine, MMP-2, MMP-7, MUC1, MUC5AC, p53, PAX5, PBF, PRAME, PSMA, RAGE-1, RGS5, RhoC, RNF43, RU2AS, SAP-1, secernin 1, SOX10, STEAP1, survivin, Telomerase, TPBG, VEGF and WT1. Other tumor antigens are encompassed by the present disclosure.

A "non-self antigen" is an antigen that originates from the external environment (outside the body). A non-self antigen is not naturally expressed in cells (normal cells or tumor cells) of a subject. With respect to a human subject, a non-self antigen may be, for example, a human antigen obtained from a different host/subject or a non-human antigen, such as a bacterial antigen, a yeast antigen, a protozoan antigen, a viral antigen. A non-self antigen may be a naturally-occurring antigen (naturally-occurring in another organisms) or a synthetic (non-naturally-occurring, e.g., artificial) antigen. Examples of non-self antigens include, without limitation, green fluorescent protein, KLH and avian ovalbumin. Engineered nucleic acids encoding non-self antigens delivered to tumor cells via a tumor-selective vehicle or intratumoral injection are expressed primarily in tumor cells and not in normal cells. Thus, immune cells genetically engineered to bind to the non-self-antigen are capable of selectively targeting tumor cells.

In some embodiments, an antigen is a peptide tag or an antigen comprises a peptide tag. Examples of peptide tags include, His tag, FLAG tag, viral peptides (e.g., CMV peptides, SV5 peptides), chitin binding protein, maltose binding protein, glutathione-S-transferase, thioredoxin, poly (NANP), V5-tag, Myc-tag, HA-tag, AviTag, calmodulin-tag, polyglutamate tag, E-tag, S-tag, SBP-tag, Softag 1, Strep-tag, TC tag, V5 tag, VSV tag, Xpress tag, isopeptag, Spytag, BCCP, Halo-tag, Nus-tag, Fc-tag and Ty tag. Other peptide tags are encompassed by the present disclosure.

Delivery Vehicles

In some embodiments, antigens are delivered to a subject via a tumor-selective vehicle. A "tumor-selective vehicle" is a molecule, agent or matrix that preferentially targets (homes to) tumor cells or, with respect to viruses and pseudoviruses, preferentially replicates in and/or infects or pseudo-infects tumor cells. In some embodiments, engineered nucleic acids of the present disclosure are encapsulated within a tumor-selective vehicle.

Examples of tumor-selective vehicles include, without limitation, viruses (including chimeric viruses and modified viruses), and pseudoviruses. Non-viral tumor-selective vehicles are also encompassed herein and described below.

A virus is a small infectious agent that replicates only inside the living cells of other organisms. A virus typically contains: (i) genetic material in the form of viral DNA or viral RNA; (ii) a protein coat, referred to as a capsid, which surrounds and protects the genetic material; and in some cases (iii) an envelope of lipids that surrounds the protein coat. A capsid, the protein shell of a virus, contains several structural subunits, each referred to as a capsomer.

Non-limiting examples of viruses of the present disclosure include oncolytic viruses and modified viruses (e.g., modified to preferentially infect tumor cells). In some embodiments, an engineered nucleic acid encoding an antigen is engineered to be part of the virus genome. In some embodiments an engineered nucleic acid encoding an antigen is encapsulated in a pseudovirus.

In some embodiments, a tumor-selective vehicle is an oncolytic virus. An oncolytic virus is a virus that preferentially infects and kills tumor cells. Examples of oncolytic viruses include, without limitation, adenoviruses, vaccinia viruses, Sindbis viruses, Seneca valley viruses, Coxsackie viruses, measles viruses, reoviruses, vaccinia viruses, Newcastle disease viruses, vesicular stomatitis viruses, herpes simplex viruses, polioviruses and parvoviruses.

In some embodiments, a tumor-selective vehicle is a targeted chimeric virus. A targeted chimeric virus is a recombinant virus containing components from at least two difference viruses. For example, a tumor-selective vehicle of the present disclosure may include a chimeric adeno-associated (AAV) and bacteriophage virus, referred to as AAVP (Hajitou A. et al. 2006 *Cell* 125: 385-398; Hajitou A. et al. 2007 *Nat. Protoc.* 2(3): 523-31; and Hajitou A. et al. 2010 *Adv. Genet.* 69: 65-82, each of which is incorporated herein by reference).

In some embodiments, a tumor-selective vehicle is a naturally-occurring virus or a virus modified to preferentially infect (target) and kills tumor cells. A non-limiting example of a virus that may be modified to target tumor cells is an adeno-associated virus (AAV). In some embodiments, the capsid of the AAV is modified (e.g., receptor targeting, mixed capsids in the shell of the virion, or marker rescue to produce recombinant virus; Chengwen L et al. 2005 *Cancer Gene Ther.* 12(12): 913-25, incorporated by reference herein). In some embodiments, a T cell-stimulating epitope of an AAV is modified.

"Pseudoviruses" are synthetic viruses used to inject genetic material, including DNA and RNA, with specific and desired traits into prokaryotic and eukaryotic cells. Pseudoviruses are closely related to viruses in structure and behavior but lack many characteristics exhibited by true viruses, including the capability to replicate. In some embodiments, an engineered nucleic acid encoding an antigen is encapsulated in a pseudovirus.

In some embodiments, a pseudovirus of the present disclosure comprises or consists of papillomavirus proteins (e.g., L1 proteins, L2 proteins, or a combination of L1 and L2 proteins). The papillomavirus proteins (L1 and L2 capsid proteins) may be human papillomavirus proteins or non-human (e.g., bovine, murine, cotton-rabbit, macaque or rhesus) papillomavirus proteins. In some embodiments, these papillomavirus proteins are modified in a way that results in the pseudovirus having a modified antigenicity relative to a pseudovirus that comprises or consists of wild-type papillomavirus proteins. For example, a modified L1 papillomavirus protein of the present disclosure may be a recombinant protein based on HPV serotype 16 and HPV serotype 31, referred to as a "modified HPV16/31 L1 protein," which is described in International Pub. No. WO/2010/120266, the entirety of which is incorporated herein by reference.

Other examples of targeting vehicles include, without limitation, natural polymers, synthetic polymers, cationic peptides, cell-penetrating peptides, biodegradable nanoparticles, liposomes, lipoplexes (e.g., PEGylated lipoplexes), polyplexes, micelles and dendrimers. In some embodiments, a synthetic delivery vehicle is a gel, a mucoadhesive or a silicon nanoneedle. Other tumor-selective vehicles are encompassed by the present disclosure.

In some embodiments, a tumor-selective vehicle is a liposome. Liposomes are spherical vesicles having at least one lipid bilayer. The term "liposome" encompasses multi-lamellar vesicles (having several lamellar phase lipid bilayers), small unilamellar liposome vesicles (having one lipid bilayer), large unilamellar vesicles and cochleate vesicles. The term "lipoplex" refers to a cationic liposome that form with DNA. The term "polyplex" refers to a polymer that forms with DNA. In some embodiments, an engineered nucleic acid encoding an antigen is encapsulated in a liposome, lipoplex or polyplex.

In some embodiments, a tumor-selective vehicle is a polymeric micelle. Polymeric micelles, by comparison, are prepared from certain amphiphilic co-polymers consisting of both hydrophilic and hydrophobic monomer units. In some embodiments, an engineered nucleic acid encoding an antigen is encapsulated in a polymeric micelle.

In some embodiments, a tumor-selective vehicle is a dendrimer. Dendrimers are also polymer-based delivery vehicles. They have a core that branches out in regular intervals to form a small, spherical and dense nanocarrier.

Delivery Routes

In some embodiments, engineered nucleic acids encoding antigens are delivered to a subject via intratumoral injection. "Intratumoral injection" is a route of administration by which an engineered nucleic acid, for example, is delivered directly to the tumor via an injection device (e.g., needle and syringe). In some embodiments, tumor-selective vehicles, immune cells, or both, are delivered to a subject via a parenteral route, an enteral route or a topical route.

Examples of parental routes include, without limitation, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (bolus or drip), intraventricular, intravesical and subcutaneous.

Enteral routes of administration include administration to the gastrointestinal tract via the mouth (oral), stomach (gastric) and rectum (rectal). Gastric administration typically involves the use of a tube through the nasal passage (NG tube) or a tube in the belly leading directly to the stomach (PEG tube). Rectal administration typically involves rectal suppositories.

Topical routes of administration include administration to a body surface, such as skin or mucous membranes. Delivery vehicles of the present disclosure may be administered topically via a cream, foam, gel, lotion or ointment, for example.

Other routes of delivery are encompassed by the present disclosure. For example, an engineered nucleic acid or a tumor-selective vehicle containing an engineered nucleic acid may be delivered via ultrasound-targeted microbubble destruction (UTMD) (Qiu L. et al. 2012 *Gene Therapy* 19: 703-710, incorporated herein by reference).

In some embodiments, an engineered nucleic acid encoding an antigen is delivered to a subject (via a tumor-selective vehicle or via intratumoral injection) prior to or after delivering an immune cell. Thus, an engineered nucleic acid and an immune cell of the present disclosure may be delivered sequentially. In other embodiments, however, an engineered nucleic acid and an immune cell are delivered simultaneously.

Immune Cells

Some embodiments of the present disclosure are directed to immune cells, such as leukocytes (nucleated white blood cells), comprising (e.g., expressing) a receptor that binds to an antigen. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T cell is a $CD4^+$ Th (T helper) cell, a $CD8^+$ cytotoxic T cell, a γδ T cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. *Transcription Factor Protocols: Methods in Molecular Biology*™ 2000; 130: 117-134), chemical (e.g., calcium phosphate or lipid), transfection (see, e.g., Lewis W. H., et al., *Somatic Cell Genet.* 1980 May; 6(3): 333-47; Chen C., et al., *Mol Cell Biol.* 1987 August; 7(8): 2745-2752), fusion with bacterial protoplasts containing recombinant plasmids (see, e.g., Schaffner W. *Proc Natl Acad Sci USA*. 1980 April; 77(4): 2163-7), microinjection of purified DNA directly into the nucleus of the cell (see, e.g., Capecchi M. R. *Cell.* 1980 November; 22(2 Pt 2): 479-88), or retrovirus transduction.

Some aspects of the present disclosure provide an "adoptive cell" approach, which involves isolating immune cells (e.g., T cells) from a subject, genetically engineering the cells (e.g., to express an antigen-binding receptor, such as a chimeric antigen receptor), expanding the cells ex vivo, and then re-introducing the cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Antigen-Binding Receptors

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A "chimeric antigen receptor" refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., *Human Gene Therapy.* 2015; 26(8):498-505).

In some embodiments, an antigen binding receptor is a chimeric antigen receptor (CAR). A T cell that expressed a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., *Human Gene Therapy.* 2015; 26(8):498-505).

There are four generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-ζ chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., *Blood*. 2015; 125(26):4017-4023; Kakarla and Gottschalk, *Cancer J.* 2014; 20(2):151-155).

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3ζ signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., *Human Gene Therapy*. 2015; 26(8):498-505; Chmielewski and Hinrich, *Expert Opinion on Biological Therapy*. 2015; 15(8): 1145-1154.

In some embodiments, a chimeric antigen receptor is a first generation CAR. In some embodiments, a chimeric antigen receptor is a third generation CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. *Molecular Therapy Nucleic Acids* 2013; 2:e105, incorporated herein by reference). Thus, methods, in some embodiments, comprise delivering to a tumor an engineered nucleic acid that encode an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. *Sci. Transl. Med.* published online Dec. 11, 2013, incorporated herein by reference). iCARs contain an antigen-specific inhibitory receptor, for example, to block nonspecific immunosuppression, which may result from extratumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., *Cytotherapy.* 2003; 5(3): 211-226; Maude et al., *Blood.* 2015; 125(26): 4017-4023, each of which is incorporated herein by reference).

Tumor Cells

The present disclosure encompasses the treatment of all types of tumors, including primary tumors and metastatic tumors. Tumors that arise from connective tissue, endothelium, mesothelium, blood cells, lymphoid cells, muscle, epithelial tissue, neural tissue and neural crest-derived cells are encompassed herein. The present disclosure also encompasses carcinomas, sarcomas, myelomas, leukemias, lymphomas, and cancers of mixed type (e.g., adenosquamous, carcinoma, mixed mesodermal tumor, carcinosarcoma and teratocarcinoma).

The following is a list of non-limiting examples of tumors/cancers encompassed by the present disclosure: acute lymphoblastic leukemia (ALL), acute myeloid leukemia (AML), adrenocortical carcinoma, AIDS-related cancers, Kaposi sarcoma, AIDS-related lymphoma, primary CNS lymphoma, anal cancer, appendix cancer, astrocytomas, atypical teratoid/rhabdoid tumor, basal cell carcinoma, bile duct cancer, bladder cancer, bone cancer, Ewing sarcoma family of tumors, osteosarcoma and malignant fibrous histiocytoma, brain stem glioma, brain tumor, astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, Burkitt lymphoma, carcinoid tumor, gastrointestinal, carcinoma of unknown primary, cardiac (heart) tumors, atypical teratoid/rhabdoid tumor, embryonal tumors, germ cell tumor, primary lymphoma, cervical cancer, cholangiocarcinoma, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, ductal carcinoma in situ (dcis), embryonal tumors, central nervous system, endometrial cancer, ependymoma, esophageal cancer, esthesioneuroblastoma, ewing sarcoma, extracranial germ cell tumor, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastrointestinal carcinoid tumor, gastrointestinal stromal tumors (gist), germ cell tumor, central nervous system, extracranial, extragonadal, ovarian, testicular, gestational trophoblastic disease, glioma, brain stem, hairy cell leukemia, head and neck cancer, heart cancer, hepatocellular (liver) cancer, histiocytosis, langerhans cell, Hodgkin lymphoma, hypopharyngeal cancer, intraocular melanoma, islet cell tumors, pancreatic neuroendocrine tumors, kaposi sarcoma, kidney, renal cell, Wilms tumor and other kidney tumors, langerhans cell histiocytosis, laryngeal cancer, acute lymphoblastic leukemia (ALL), acute myeloid leukemia (AML), chronic lymphocytic leukemia (CLL), chronic myeloid leukemia (CML), hairy cell, lip and oral cavity cancer, liver cancer (primary), lung cancer, non-small cell, small cell, lymphoma, Burkitt, cutaneous t-cell, Hodgkin, non-Hodgkin, primary central nervous system (CNS), macroglobulinemia, waldenstrom, male breast cancer, malignant fibrous histiocytoma of bone and osteosarcoma, melanoma, intraocular (eye), merkel cell carcinoma, mesothelioma, malignant, metastatic squamous neck cancer with occult primary, midline tract carcinoma involving nut gene, mouth cancer, multiple endocrine neoplasia syndromes, multiple myeloma/plasma cell neoplasm, mycosis fungoides, myelodysplastic syndromes, myelodysplastic/myeloproliferative neoplasms, myelogenous leukemia, myeloma, myeloproliferative neoplasms, chronic, nasal cavity and paranasal sinus cancer, nasopharyngeal cancer, neuroblastoma, non-Hodgkin lymphoma, non-small cell lung cancer, ocular, oral cancer, oral cavity cancer, lip and, oropharyngeal cancer, osteosarcoma and malignant fibrous histiocytoma of bone, ovarian cancer, epithelial, germ cell tumor, low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, renal pelvis and ureter, transitional cell cancer, retinal cancer, retinoblastoma, rhabdomyosarcoma, salivary gland cancer, sarcoma, ewing, kaposi, osteosarcoma (bone cancer), rhabdomyosarcoma, soft tissue, uterine, Sézary syndrome, skin cancer, melanoma, merkel cell carcinoma, nonmelanoma, small cell lung cancer, small intestine cancer, soft tissue sarcoma, squamous cell carcinoma, squamous neck cancer with occult primary, metastatic, stomach (gastric) cancer, t-cell lymphoma, cutaneous, testicular cancer, throat cancer, thymoma and thymic carcinoma, thyroid cancer, transitional cell cancer of the renal pelvis and ureter, unknown primary, carcinoma of, unusual cancers of, ureter and renal pelvis, transitional cell cancer, urethral cancer, uterine cancer, endometrial, uterine sarcoma, vaginal cancer, vulvar cancer and waldenstrom macroglobulinemia.

Nucleic Acids

Some embodiments of the present disclosure are directed to nucleic acids encoding antigens (e.g., non-self antigens). Such nucleic acids are delivered to a subject and targeted to tumor cells (e.g., via a tumor-selective vehicle or intratumoral injection) where the nucleic acid is expressed (e.g., overexpressed) in the tumor cells. In some embodiments, a nucleic acid encoding an antigen is a deoxyribonucleic acid (DNA) or a ribonucleic acid (RNA), such as a messenger RNA (mRNA). Nucleic acids of the present disclosure, in some embodiments, are engineered nucleic acids. An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphosphoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Delivery of modified mRNA is also encompassed by the present disclosure. Modified mRNA includes, for example, mRNA modified for improved codon usage, stability and antigen-processing characteristics of the encoded protein.

Engineered nucleic acids of the present disclosure may be produced using standard molecular biology methods (see, e.g., *Green and Sambrook, Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Expression of engineered nucleic acids is typically driven by a promoter operably linked to the engineered nucleic acid. A "promoter" refers to a control region of a nucleic acid at which initiation and rate of transcription of the remainder of a nucleic acid sequence are controlled. A promoter drives transcription or of the nucleic acid sequence that it regulates, thus, it is typically located at or near the transcriptional start site of a gene. A promoter, in some embodiments, is 100 to 1000 nucleotides in length. A promoter may also contain sub-regions at which regulatory proteins and other molecules may bind, such as RNA polymerase and other transcription factors. Promoters may be constitutive, inducible (also referred to as activatable), repressible, tissue-specific, developmental stage-specific or any combination of two or more of the foregoing. Examples of constitutive promoter for use in accordance with the present disclosure include, without limitation, the CAG promoter (containing a cytomegalovirus (CMV) early enhancer element, a promoter obtained from the first exon and the first intron of chicken beta-actin gene, and a splice acceptor of the rabbit beta-globin gene), the CMV promoter, and the tumor-specific Grp78 promoter (Kia A. 2012 *Mol. Cancer Ther.* 11(12): 2566-77, incorporated herein by reference).

A promoter is considered to be "operably linked" when it is in a correct functional location and orientation relative to a sequence of nucleic acid that it regulates (e.g., to control ("drive") transcriptional initiation and/or expression of that sequence).

A promoter, in some embodiments, is naturally associated with a nucleic acid and may be obtained by isolating the 5' non-coding sequence(s) located upstream of the coding region of the given nucleic acid. Such a promoter is referred to as an "endogenous" promoter.

A promoter, in some embodiments, is not naturally associated with a nucleic acid. Such a promoter is referred to as a "heterologous" promoter and includes, for example, promoters that regulate other nucleic acids and promoters obtained from other cells. A heterologous promoter may be synthetic or recombinant. Synthetic heterologous promoters, in some embodiments, contain various elements obtained from known transcriptional regulatory regions. Synthetic heterologous promoters, in some embodiments, contain mutations that alter expression through methods of genetic engineering that are known in the art. Recombinant heterologous promoters, in some embodiments, are produced by recombinant cloning, nucleic acid amplification (e.g., polymerase chain reaction (PCR)), or a combination of recombinant cloning and nucleic acid amplification (see U.S. Pat. Nos. 4,683,202 and 5,928,906). Other methods of producing synthetic and recombinant heterologous promoters are contemplated herein.

A promoter, in some embodiments, is an inducible promoter. An "inducible promoter" regulates (e.g., activates or inactivates) transcriptional activity of a nucleic acid to which it is operably linked when the promoter is influenced by or contacted by a corresponding regulatory protein.

Thus, a "regulatory protein," as used herein, is a protein that modulates (e.g., activates or inactivates) transcriptional activity from a promoter (e.g., an inducible promoter). In some embodiments, a regulatory protein binds directly to an inducible promoter (e.g., to a sequence of nucleotides within a promoter). In some embodiments, a regulatory binds to a region upstream from an inducible promoter (e.g., within 50 to 100 nucleotides upstream from an inducible promoter). In some embodiments, a regulatory protein binds proximal to (e.g., adjacent to) an inducible promoter. Examples of regulatory proteins include, without limitation, tetracycline-controlled transactivator (tTA) transcription factor, reverse tetracycline-controlled transactivator (rtTA) transcription factor, and Lac repressor protein.

In some embodiments, a nucleic acid encoding an antigen is overexpressed or misexpressed in a tumor cell. A nucleic acid or protein is considered "overexpressed" if its levels of expression exceed (e.g., by at least 10%, 50%, 100%, 200%, or more) its normal (wild-type) level of expression. A nucleic acid or protein is considered "misexpressed" if it is expressed in a cell or in a compartment of a cell in which it is not normally expressed.

Additional Embodiments

Additional embodiments of the present disclosure are encompassed by the following number paragraphs:
1. A method comprising delivering to a subject an engineered nucleic acid encoding an antigen, wherein the engineered nucleic acid is delivered via a tumor-selective vehicle or via intratumoral injection, and delivering to the subject an immune cell expressing a receptor that binds to the antigen.
2. The method of paragraph 1, wherein the antigen is a self-antigen, a non-self antigen, or a combination thereof.
3. The method of paragraph 2, wherein the antigen is a non-self antigen.
4. The method of paragraph 3, wherein the non-self antigen is a bacterial, yeast, protozoan or viral antigen.
5. The method of paragraph 3, wherein the non-self antigen is a synthetic antigen 6. The method of paragraph 1 or 2, wherein the antigen is a tumor antigen.
7. The method of paragraph 6, wherein the tumor antigen is a tumor-specific antigen (TSA) or a tumor-associated antigen (TAA).
8. The method of paragraph 6, wherein the tumor antigen is or comprises an epitope of CD19, CD20, CD21, CD22, CD45, BCMA, MART-1, MAGE-A3, glycoprotein 100 (gp100), NY-ESO-1, HER2 (ErbB2), IGF2B3, EGFRvIII, Kallikrein 4, KIF20A, Lengsin, Meloe, MUC-1, MUCSAC, MUC-16, B7-H3, B7-H6, CD70, CEA, CSPG4, EphA2, EpCAM, EGFR family, FAP, FRα, glupican-3, GD2, GD3, HLA-A1+MAGE1, IL-11Rα, IL-23Rα2, Lewis-Y, mesothelin, NKG2D ligands, PSMA, ROR1, survivin, TAG72 or VEGFR2.
9. The method of paragraph 8, wherein the tumor antigen is or comprises an epitope of CD19.
10. The method of paragraph 9, wherein the tumor antigen is selected from full length CD19, a fragment of CD19, at least one C2 Ig-like domain of CD19, or a linear epitope of CD19.
11. The method of any one of paragraphs 1-10, wherein the engineered nucleic acid encoding the antigen is encapsulated within the tumor-selective vehicle.
12. The method of any one of paragraphs 1-11, wherein tumor-selective vehicle is a virus or a pseudovirus.
13. The method of paragraph 12, wherein the tumor-selective vehicle is an oncolytic virus.
14. The method of paragraph 13, wherein the oncolytic virus is an adenovirus, a vaccinia virus, a Sindbis virus, a Seneca valley virus, a Coxsackie virus, a measles virus, a reovirus, a vaccinia virus, a Newcastle disease virus, a vesicular stomatitis virus, a herpes simplex virus, a poliovirus, or a parvovirus.
15. The method of paragraph 12, wherein the tumor-selective vehicle is a chimeric virus.
16. The method of paragraph 15, wherein the chimeric virus is obtained from engineering adeno-associated viruses and bacteriophages that display tumor selective peptides.
17. The method of paragraph 12, wherein the tumor-selective vehicle is a virus that is modified to target tumor cells.
18. The method of paragraph 12, wherein the tumor-selective vehicle is an adeno-associated virus (AAV) that is modified to target tumor cells.
19. The method of paragraph 12, wherein the tumor-selective vehicle is a papillomavirus.
20. The method of paragraph 19, wherein the papillomavirus is a human papillomavirus.
21. The method of paragraph 19, wherein the papillomavirus is a modified human papillomavirus.
22. The method of paragraph 19, wherein the papillomavirus is a non-human papillomavirus.
23. The method of paragraph 22, wherein the papillomavirus is a modified non-human papillomavirus.
24. The method of paragraph 12, wherein the tumor-selective vehicle is a pseudovirus.
25. The method of any one of paragraphs 1-11, wherein tumor-selective vehicle is or comprises a natural polymer, a synthetic polymer, a cationic peptide, a cell-penetrating peptide, a biodegradable nanoparticle, a liposome, a lipoplex, a polyplex, a micelle, a dendrimer, a gel, a mucoadhesive or a silicon nanoneedle.
26. The method of any one of paragraphs 1-25, wherein the tumor-selective vehicle comprises a tumor-targeting agent.
27. The method of any one of paragraphs 1-26, wherein the engineered nucleic acid encoding an antigen is a deoxyribonucleic acid (DNA).
28. The method of any one of paragraphs 1-26, wherein the engineered nucleic acid encoding an antigen is a ribonucleic acid (RNA).
29. The method of paragraph 28, wherein the RNA is a messenger RNA (mRNA).
30. The method of any one of paragraphs 1-29, wherein the immune cell is leukocyte.
31. The method of paragraph 30, wherein the leukocyte is a neutrophil, eosinophil, basophil, lymphocyte or a monocyte.
32. The method of paragraph 31, wherein the leukocyte is a lymphocyte.
33. The method of paragraph 32, wherein the lymphocyte is a T cell, a B cell, an NK cell, or an NKT cell.
34. The method of paragraph 33, wherein the lymphocyte is a T cell.
35. The method of any one of paragraphs 1-29, wherein immune cell is a dendritic cell.
36. The method of any one of paragraphs 1-35, wherein the receptor is a recombinant antigen receptor.
37. The method of any one of paragraphs 1-35, wherein the receptor is a chimeric antigen receptor.
38. The method of any one of paragraphs 1-37, wherein the tumor-selective vehicle is delivered via a parenteral, enteric or topical route.
39. The method of paragraph 38, wherein the parenteral route is intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (bolus or drip), intraventricular, intravesical or subcutaneous.
40. The method of any one of paragraphs 1-38, wherein the engineered nucleic acid is injected into the tumor.
41. The method of any one of paragraphs 1-40, wherein the method comprises delivering to a subject at least two engineered nucleic acids, each encoding a different antigen.
42. A method comprising delivering to a subject an engineered nucleic acid that induces expression of a self-antigen, wherein the engineered nucleic acid is delivered via a tumor-selective vehicle or via intratumoral injection, and delivering to the subject an immune cell expressing a receptor that binds to the self-antigen.

43. The method of paragraph 42, wherein the self-antigen is a tumor antigen.

44. The method of paragraph 43, wherein the tumor antigen is a tumor-specific antigen (TSA) or a tumor-associated antigen (TAA).

45. The method of paragraph 44, wherein the tumor antigen is or comprises an epitope of CD19, CD20, CD21, CD22, CD45, BCMA, MART-1, MAGE-A3, glycoprotein 100 (gp100), NY-ESO-1, HER2 (ErbB2), IGF2B3, EGFRvIII, Kallikrein 4, KIF20A, Lengsin, Meloe, MUC-1, MUC5AC, MUC-16, B7-H3, B7-H6, CD70, CEA, CSPG4, EphA2, EpCAM, EGFR family, FAP, FRα, glupican-3, GD2, GD3, HLA-A1+MAGE1, IL-11Rα, IL-23Rα2, Lewis-Y, mesothelin, NKG2D ligands, PSMA, ROR1, survivin, TAG72 or VEGFR2.

46. The method of paragraph 44, wherein the tumor antigen is or comprises a peptide tag.

47. The method of paragraph 46, wherein the peptide tag is selected from the group consisting of His tag, FLAG tag, CMV peptide, SV5 peptide, chitin binding protein, maltose binding protein, glutathione-S-transferase, thioredoxin, poly (NANP), V5-tag, Myc-tag, HA-tag, AviTag, calmodulin-tag, polyglutamate tag, E-tag, S-tag, SBP-tag, Softag 1, Streptag, TC tag, V5 tag, VSV tag, Xpress tag, isopeptag, Spytag, BCCP, Halo-tag, Nus-tag, Fc-tag and Ty tag.

48. The method of any one of paragraphs 42-47, wherein the engineered nucleic acid that induces expression of a self-antigen is encapsulated within the tumor-selective vehicle.

49. The method of any one of paragraphs 42-48, wherein tumor-selective vehicle is a virus, a virus-like particle or a pseudovirus.

50. The method of paragraph 49, wherein the tumor-selective vehicle is an oncolytic virus.

51. The method of paragraph 50, wherein the oncolytic virus is an adenovirus, a vaccinia virus, a Sindbis virus, a Seneca valley virus, a Coxsackie virus, a measles virus, a reovirus, a vaccinia virus, a Newcastle disease virus, a vesicular stomatitis virus, a herpes simplex virus, a poliovirus, or a parvovirus.

52. The method of paragraph 49, wherein the tumor-selective vehicle is a chimeric virus.

53. The method of paragraph 52, wherein the chimeric virus is obtained from engineering adeno-associated viruses and bacteriophages that display tumor selective peptides.

54. The method of paragraph 49, wherein the tumor-selective vehicle is a virus that is modified to target tumor cells.

55. The method of paragraph 49, wherein the tumor-selective vehicle is an adeno-associated virus (AAV) that is modified to target tumor cells.

56. The method of paragraph 49, wherein the tumor-selective vehicle is a papillomavirus.

57. The method of paragraph 56, wherein the papillomavirus is a human papillomavirus.

58. The method of paragraph 56, wherein the papillomavirus is a modified human papillomavirus.

59. The method of paragraph 56, wherein the papillomavirus is a non-human papillomavirus.

60. The method of paragraph 59, wherein the papillomavirus is a modified non-human papillomavirus is a bovine papillomavirus.

61. The method of paragraph 49, wherein the tumor-selective vehicle is a virus-like particle.

62. The method of paragraph 49, wherein the tumor-selective vehicle is a pseudovirus.

63. The method of any one of paragraphs 42-48, wherein tumor-selective vehicle is or comprises a natural polymer, a synthetic polymer, a cationic peptide, a cell-penetrating peptide, a biodegradable nanoparticle, a liposome, a lipoplex, a polyplex, a micelle, a dendrimer, a gel, a mucoadhesive or a silicon nanoneedle.

64. The method of any one of paragraphs 42-63, wherein the tumor-selective vehicle comprises a tumor-targeting agent.

65. The method of any one of paragraphs 42-64, wherein the engineered nucleic acid that induces expression of the self-antigen is a deoxyribonucleic acid (DNA).

66. The method of any one of paragraphs 42-64, wherein the engineered nucleic acid that induces expression of the self-antigen is a ribonucleic acid (RNA).

67. The method of paragraph 66, wherein the RNA is a messenger RNA (mRNA).

68. The method of paragraph 66, wherein the engineered nucleic acid that induces expression of the self-antigen is a regulatory RNA or encodes a regulatory protein.

69. The method of paragraph 65, wherein the engineered nucleic acid that induces expression of the self-antigen contains a promoter.

70. The method of paragraph 69, wherein the promoter is a natural promoter.

71. The method of paragraph 69, wherein the promoter is a recombinant promoter.

72. The method of paragraph 69, wherein the promoter is a constitutive promoter.

73. The method of paragraph 72, wherein the constitutive promoter is a CMV promoter.

74. The method of paragraph 69, wherein the promoter is an inducible promoter.

75. The method of paragraph 69, wherein the promoter is a tissue-specific promoter.

76. The method of any one of paragraphs 42-75, wherein the immune cell is leukocyte.

77. The method of paragraph 76, wherein the leukocyte is a neutrophil, eosinophil, basophil, lymphocyte or a monocyte.

78. The method of paragraph 77, wherein the leukocyte is a lymphocyte.

79. The method of paragraph 78, wherein the lymphocyte is a T cell, a B cell, an NK cell, or an NKT cell.

80 The method of paragraph 79, wherein the lymphocyte is a T cell.

81. The method of any one of paragraphs 42-75, wherein immune cell is a dendritic cell.

82. The method of any one of paragraphs 42-81, wherein the receptor is a chimeric antigen receptor.

83. The method of any one of paragraphs 42-82, wherein the tumor-selective vehicle is delivered via a parenteral, enteric or topical route.

84. The method of paragraph 83, wherein the parenteral route is intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratympanic, intrauterine, intravascular, intravenous (bolus or drip), intraventricular, intravesical or subcutaneous.

85. The method of any one of paragraphs 42-83, wherein the engineered nucleic acid is injected into the tumor.

86. A method comprising delivering to a tumor an engineered nucleic acid that encode an antigen, or delivering to a tumor an engineered nucleic acid that induces expression of a self-antigen, and delivering to the tumor an immune cell expressing a bispecific antigen receptor that binds to the two antigens.

87. The method of paragraph 86, wherein the bispecific antigen receptor is a bispecific T cell receptor or a bispecific chimeric antigen receptor.

88. The method of paragraph 87, wherein the bispecific antigen receptor also binds to a self-antigen naturally expressed by the tumor.

89. The method of paragraph 87, wherein the bispecific antigen receptor also binds to a non-tumor antigen present on a monocyte and provides an inhibitory signal.

90. A method comprising delivering to a tumor two engineered nucleic acid that encode two different antigens, or delivering to a tumor two engineered nucleic acid that induce expression of two different self-antigens, and delivering to the tumor an immune cell expressing two different antigen receptors that respectively bind to each of the two different antigens.

91. The method of paragraph 90, wherein the two different antigen receptors are recombinant T cell receptors or chimeric antigen receptors.

92. The method of any one of paragraphs 1-91, wherein the tumor is an ocular tumor, a melanoma, a head and neck tumor, a lung tumor, a bladder tumor, a breast tumor, a colorectal tumor, a gastric tumor, an ovarian tumor, a pancreatic tumor, a prostate tumor, a liver tumor, or a renal tumor.

The present disclosure is further illustrated by the following Example, which in no way should be construed as further limiting.

EXAMPLES

Example 1: Papillomavirus Pseudovirions (PsV) Production

This and the following examples discuss methods involving delivery of papillomavirus (PV) PsV comprising nucleic acid encoding CD19 as an antigen on tumor cells and targeting these CD19-expressing tumor cells with CAR T cells that express a receptor that recognizes and binds CD19. FIG. 1 depicts components for such a treatment method. The objective is to target tumors in a subject using PV pseudovirions expressing cDNA encoding CD19, and then administer to the subject T cells, derived from the subject, that have been engineered to express a chimeric antigen receipt (CAR) containing an scFv antibody fragment that binds specifically to CD19.

Figure 2:
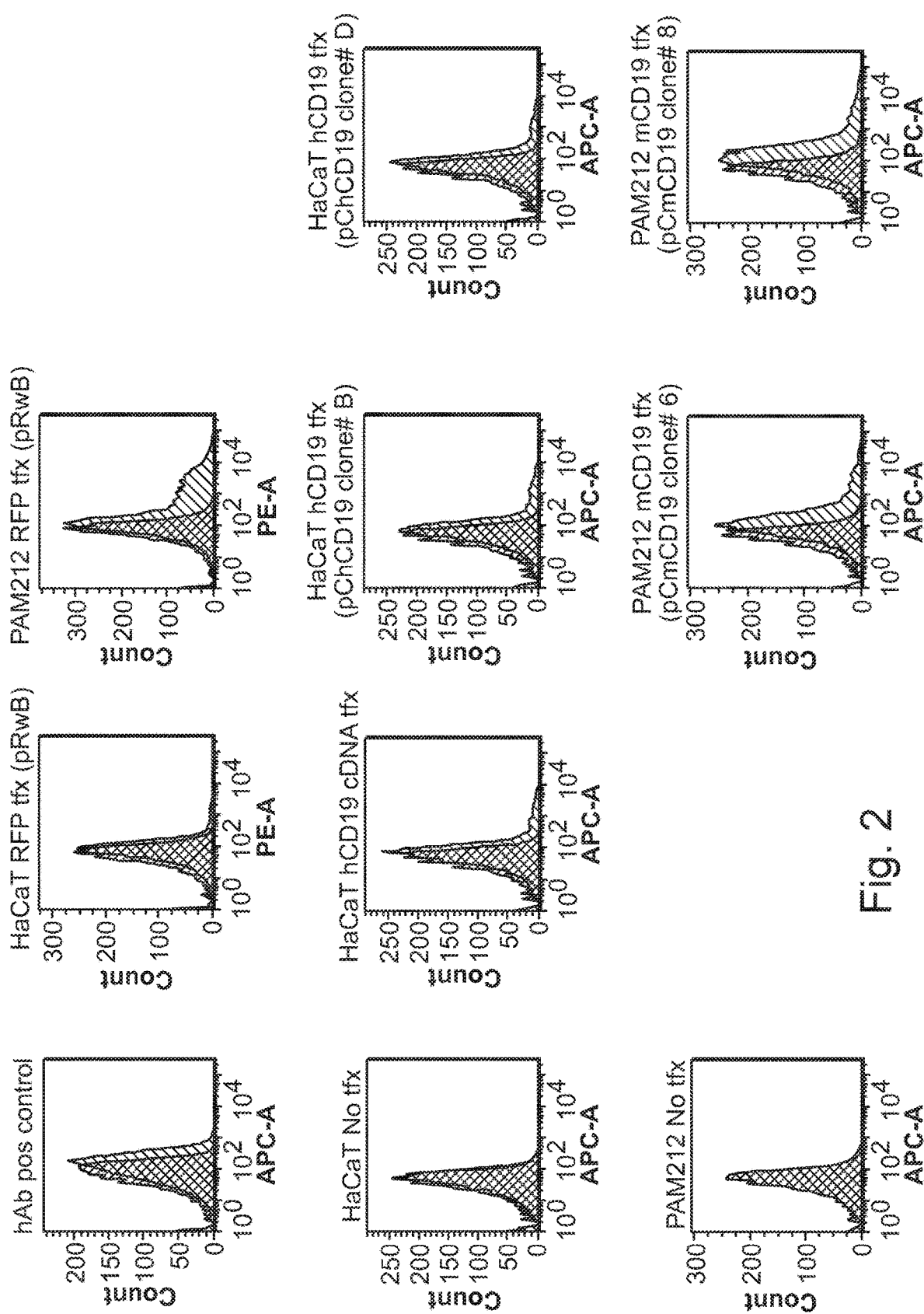
FIG. 2 shows results of CD19 expression in HaCaT human keratinocyte and PAM212 mouse keratinocyte cells following transfection of CD19 expression vector clones (clones #B and #D, and clones #6 and #8 for human and mouse CD19, respectively). Transfection with a red fluorescent protein (RFP) expression vector was used as a positive controls, and non-transfected cells were used as negative controls.

Human and mouse keratinocyte HaCaT and PAM212 were used to initially validate expression of the corresponding CD19 gene from the expression vectors after plasmid DNA transfection. FIG. 2 provides confirmation of expression of CD19 after transfection of vector clones in HaCaT human keratinocyte and PAP212 mouse keratinocyte cells.

Figure 3A:
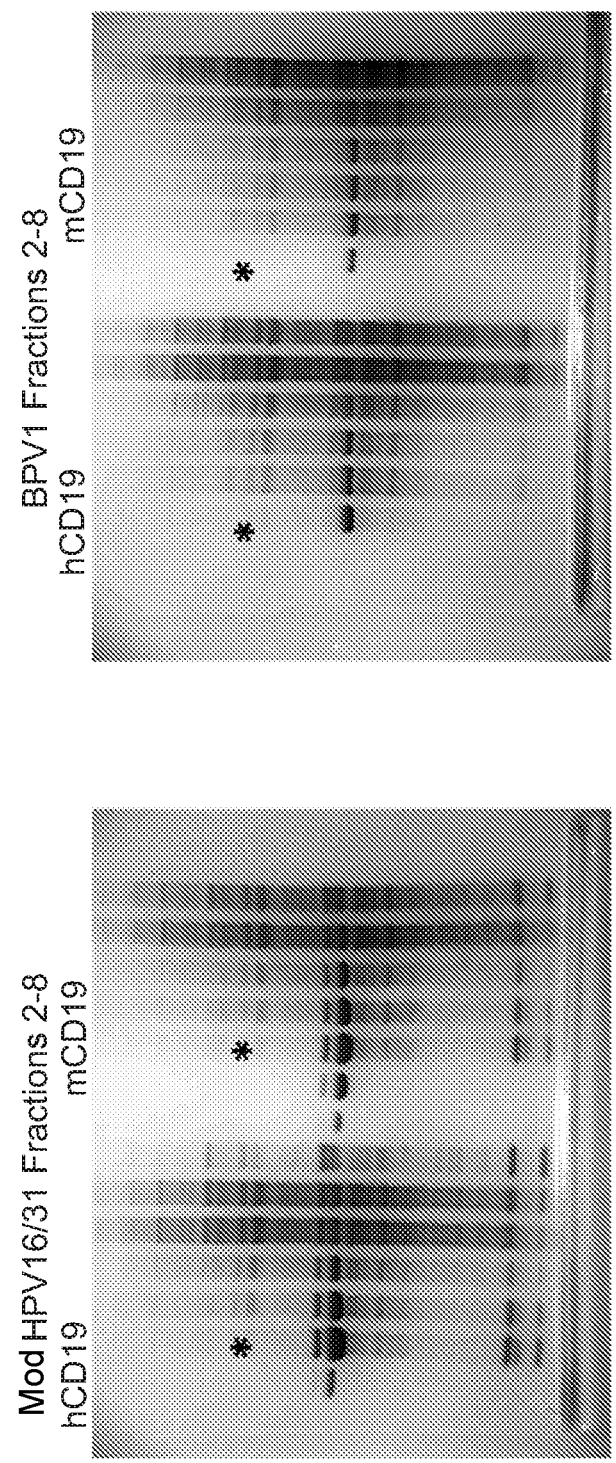
FIG. 3A (right image) is an electrophoretic gel image showing purification fractions obtained from cell lysates of 293TT cells transfected with two DNA expression vectors: modified HPV16/31 L1/L2 and (human) hCD19 (clone #B, see FIG. 2) or (mouse) mCD19 (clone #6, see FIG. 2). The modified L1 and L2 proteins are expressed and self-assemble preferentially encapsidating the CD19 expression vector to generate PsV. After two days, cells are lysed and the PsV is purified using density centrifugation and fractions are collected (PsV production and purification described in Buck 2007).
Figure 3B:
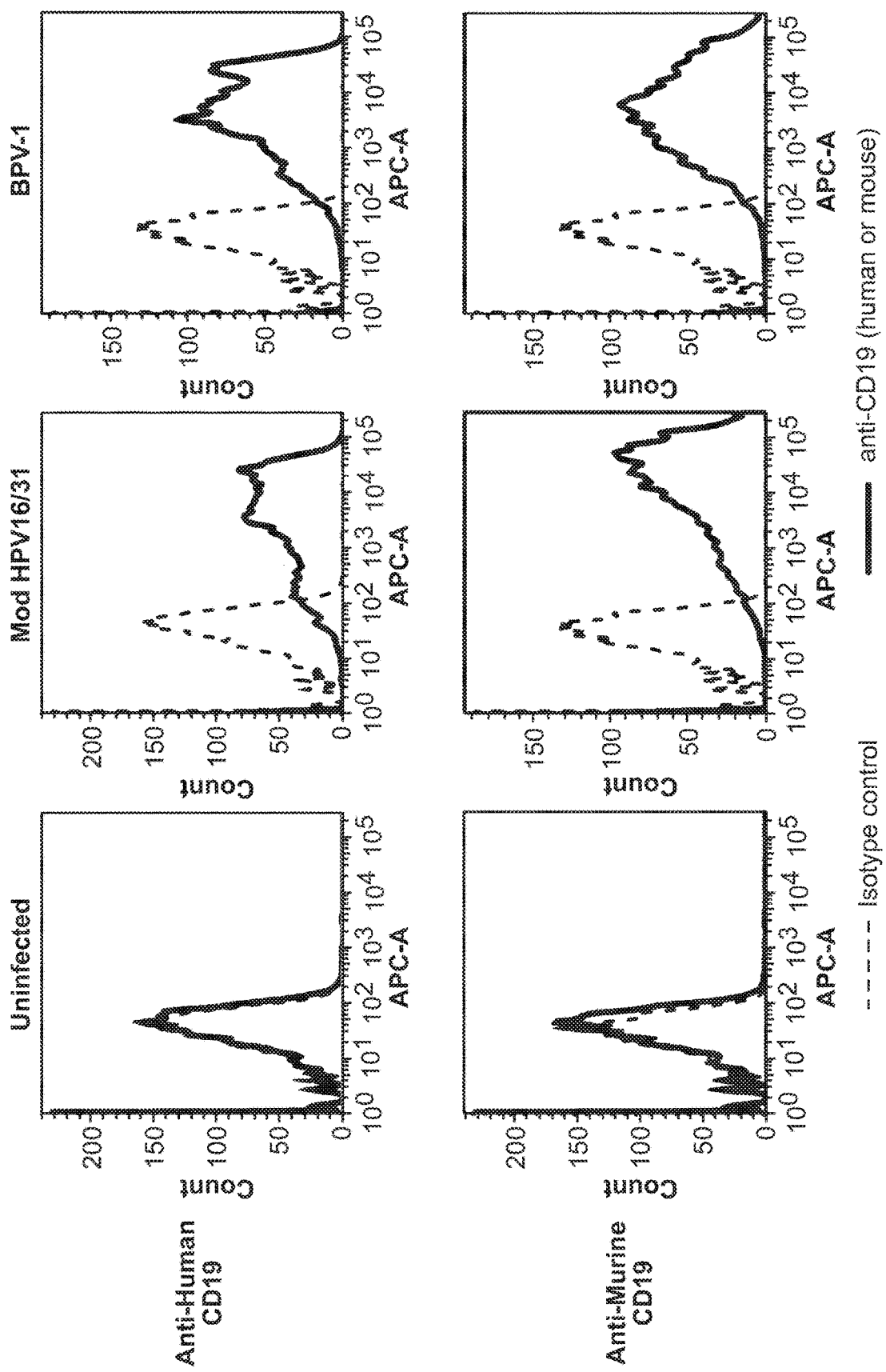
FIG. 3B shows graphs demonstrating CD19 expression in 293TT cells infected with fractions (denoted by * in FIG. 3A) of PsV that carry nucleic acid encoding CD19. 1 µl of the fractions for modified HPV16/31 PsV and BPV PsV were used for infection.

CD19 vector clones #B and #6 of human and mouse CD19, respectively, were then co-transfected with a vector encoding PV L1 and L2 proteins to produce PsV that encapsidated nucleic acid encoding CD19, as described below. 293TT cells were cultured in a T225 tissue culture flask for each PsV (modified HPV16/31 or BPV) for each CD19 construct. FIG. 3A shows the optiprep purification fractions of the lysed cells. Fractions identified as optimal (high virion content with high purity) were selected for use. Confirmation of CD19 surface expression in cells containing PsV in the optimal fractions is shown in FIG. 3B.

Materials and Methods

Generation of CD19 Expression Vectors

Human CD19 (hCD19; Accession: NM_001770) and murine CD19 (mCD19; Accession: NM_009844) cDNA sequences were purchased in pCMV6 vectors (OriGene). They were then cloned into a pCI based vector driven by the CMV promoter and containing a gene encoding green fluorescent protein (GFP). The cloning was as follows: the luciferase gene of plasmid pCLucF (home.ccr.cancer.gov/lco/pCLucf.htm) was removed with EcoRI and NotI. In the case of murine CD19, the vector was blunted prior to NotI digestion. hCD19 was removed from pCMV6-XL5 with EcoRI and NotI and ligated into the vector. mCD19 was removed from pCMV6-Entry with PvuI, blunted and then digested with NotI prior to ligation into the vector. Sequencing of clones was first performed using promoters within the CMV promoter and the poly A region, and from here two clones were then sent for internal sequencing using the primers of SEQ ID NO: 1-4.

Primers for Sequencing CD19 Expression Vectors

```
                                         (SEQ ID NO: 1)
        AGCTGTATGTGTGGGC (SEQ ID NO: 2)
        GCTCCACACTTTGGCTGT (SEQ ID NO: 3)
        CTTCAAAGTGACGCCTCC (SEQ ID NO: 4)
        TCTATGAGAACGACTCC
```

PsV Production of Modified HPV16/31 and BPV-1

PsV, which packaged target plasmids encoding the cDNA for the target tumor antigen (e.g., encoding human CD19 protein), were made. The PsV were generated as described in Buck and Thompson (2007). Briefly, a large plasmid (>8 Kb) co-expressing the viral coat proteins (L1 and L2) was co-transfected with the antigen expressing target plasmid (<8 Kb; e.g., expressing human CD19 protein) into 293TT cells. The cDNAs to be packaged were cloned into mammalian expression vector plasmids based on the pCI-neo backbone using standard molecular cloning techniques. Multiple proteins can be encoded on the same or individual plasmids and in this instance, both CD19 expression vectors also express green fluorescent protein (GFP). Over 48 hours, the viral coat proteins L1 and L2 proteins self-assembled into partially-assembled particles or protocapsids and encapsidated the target plasmid, preferentially packaging it due to its size. After 48 hours, the cells were lysed, and the partially-assembled particles or protocapsids were further matured and purified by density ultracentrifugation, as described in Buck and Thompson (2007). An optiprep density gradient can be used for purification.

293TT Gene Transduction ("Infection") and Detection of Surface Expressed CD19

$2 \times 10^4$ 293 TT cells were pre-plated in 500 µl of media in a 24-well plate and allowed to incubate overnight. After 24 hr, 1 µl of the pseudovirus preparations were added to the cells and allowed to incubate for 48 hr. Cells were then detached from the plates using 10 mM EDTA, washed with PBS+2% FBS and stained for surface expression of CD19 using the following antibodies: anti-human CD19 APC, Clone SJ25C1 Biolegend Cat #363006, 5 ul/$10^6$ cells; anti-mouse CD19 APC, Clone 6D5 Biolegend Cat #115512, 1:100/$10^6$ cells. Uninfected cells were stained with the antibodies, and infected cells were stained with isotype-matched antibodies in order to serve as background controls. Cells were acquired on a BD Facs Canto II and the data were analyzed in FlowJo V10. Data were reported as histograms showing raw cell counts as determined by fluorescent intensity of the surface bound antibody.

Example 2: In Vitro Validation of Infectivity and Surface Expression of Antigen CD19

PsV Delivered Tumor Antigen

Figure 4A:
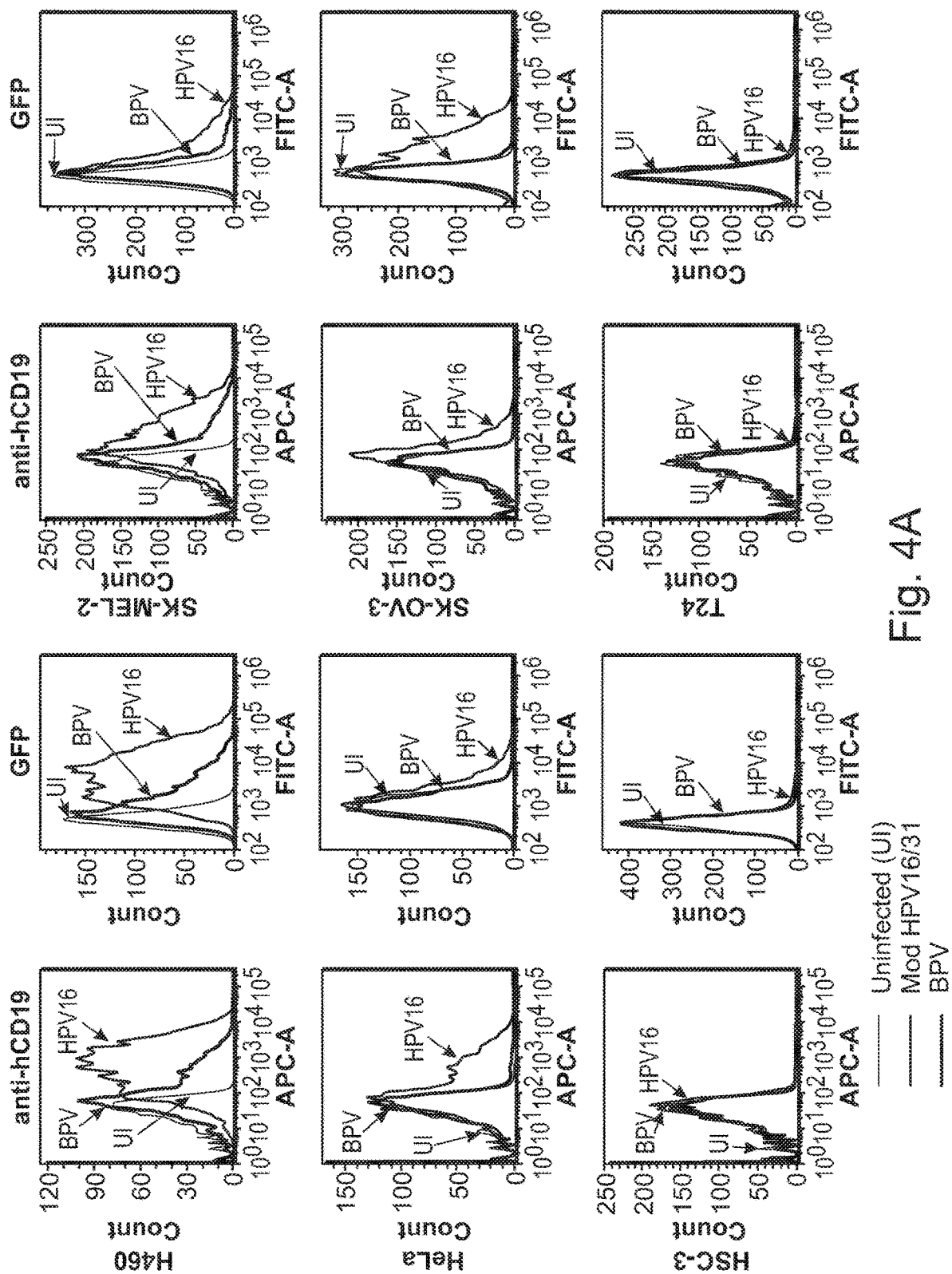
FIGS. 4A and 4B show confirmation of infection and surface expression of human CD19 in tumor cells of various cancer types after infection with modified HPV16/31 PsV or BPV PsV, each containing nucleic acid encoding hCD19.
Figure 4B:
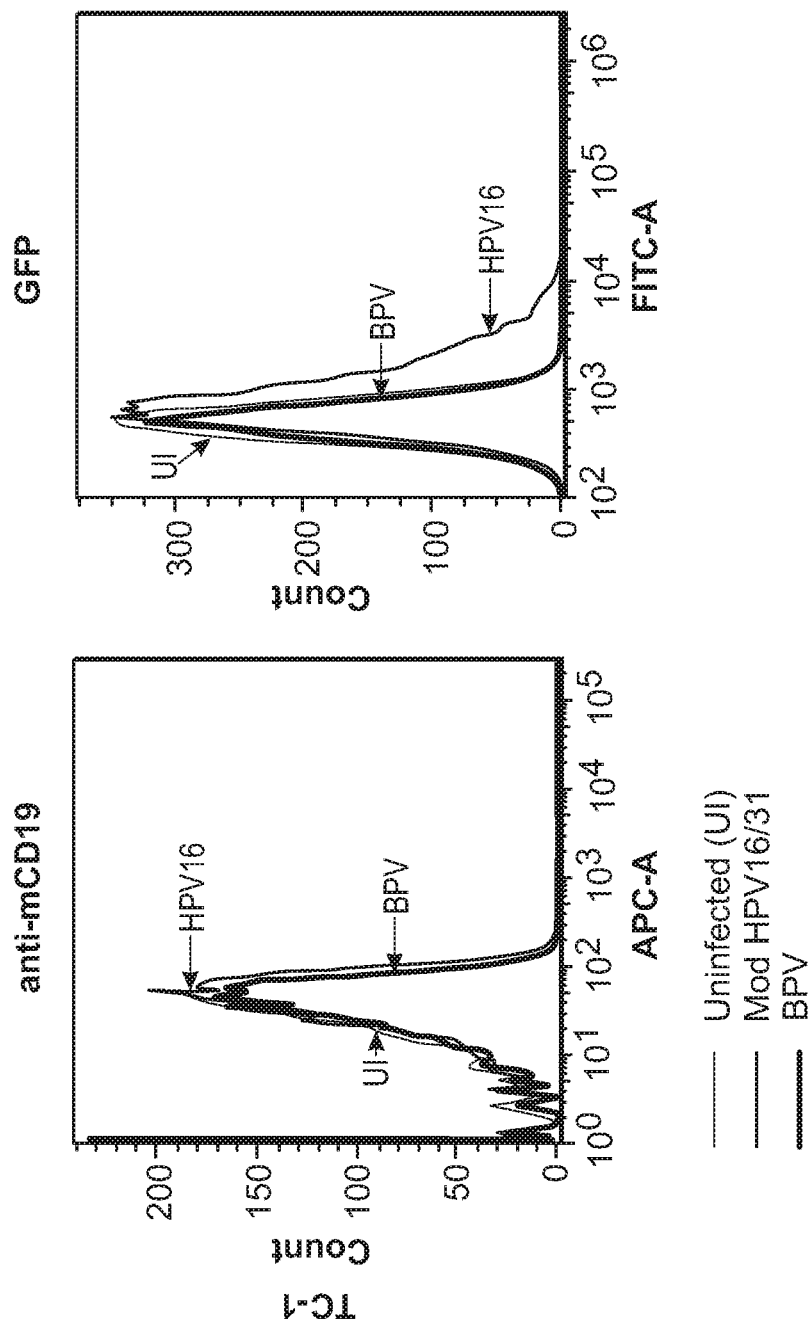

Tumor cells were pre-plated overnight at low density ($2\times10^4$). Cells were then treated with 1 µl of PsV at 37° C. After 48 hours, cells were harvested by dissociation and cell surface expression of the tumor antigen (e.g., CD19) was measured by immunofluorescent detection using fluorophore-conjugated antibodies directed against the antigen followed by detection using flow cytometry. FIGS. 4A and 4B show surface expression of CD19 in cells of different lineage that were infected with modified HPV16/31 PsV or BPV PsV carrying nucleic acid encoding human CD19 or mouse CD19, as described in Example 1. FIG. 4A shows cells of various human cancer types successfully infected by PsV carrying nucleic acid encoding human CD19 cells. Modified HVP16/31 PsV infected H460 large cell lung cancer cells, HeLa cervical cancer cells, SK-MEL-2 melanoma cells and SK-OV-3 ovarian carcinoma cells more efficiently than BPV PsV. Efficiency of both modified HVP16/31 PsV and BPV PsV is comparable for HSC-3 oral cancer cells and T24 bladder carcinoma cells. FIG. 4B shows murine tumor cells, TC-1, infected by PsV carrying nucleic acid encoding mouse CD19 however expression was below the detection threshold despite evidence for successful gene delivery as demonstrated by GFP expression.

Example 3: In Vitro Targeting of Antigen Expressing Tumor Cells with Antigen-Specific CAR T Cells Surface expression of antigen on tumor cells is validated, and antigen-specific CAR T cells are co-cultured with the transduced target tumor cells at varying ratios (e.g., 1:1, 1:5, 5:1, 10:1, 1:10). Tumor cells of various cancers are tested. After two days, supernatant and cells are harvested to measure cytokine production and cell viability. Inclusion of non-specific T cells and/or non-infected tumor cells as controls demonstrates that the targeted tumor cells are killed in a CAR-specific and PsV-specific manner.

Example 4: In Vivo Validation of Targeting of Antigen Expressing Tumor Cells with Antigen-Specific CAR T Cells PsV Delivered Tumor Antigen Syngeneic or xenograft tumors are established in matched mouse strains or immunodeficient (e.g., NOD/SCID) mice and are allowed to grow until palpable tumors are obtained. Xenograft tumors will include human tumor cell lines, patient derived (PDX) cell lines and/or primary human patient tumors. Mice with tumors of 50-100 mm$^3$ are randomized for treatment. The optimal concentration of PsV is administered IV, IP or intratumorally (IT). Two days later, CAR T-cells ($10^5$-$10^9$) are injected via various routes, preferably IV, IP or IT. Tumor volumes and mouse survival are measured. In additional experiments, tumor volume is allowed to exceed 100 mm$^3$ (e.g., 200-500 mm$^3$) in order to measure tumor regression in the presence of CAR T cell therapy. An example of a tumor model is a xenograft model of ovarian cancer. For an established ovarian cancer model, 6- to 12-week-old female NOD/SCID or NOD/SCID/common gamma chain deficient mice are inoculated subcutaneously with $1\times10^6$ A1847, SKOV3 or OVCAR (e.g., lines 2, 3, or 5) cells on the flank on day 0. After tumors become palpable at about 6 weeks, human primary T cells, or placenta-derived multipotent cells (PDMCs) are activated, and transduced with the lentiviral CAR expression vectors as described. After 2 weeks of T cell expansion, the tumor burden will be >100 mm$^3$. Mice are then injected IV, IP or IT with the optimal amount of PsV, followed two days later by an IV injection of CAR T cells. For the intraperitoneal model of ovarian cancer, 6 to 12-week-old NOD/SCID or NOD/SCID/common gamma chain deficient mice are injected IP with $10\times10^6$ A1847, SKOV3 or OVCAR (e.g., lines 2, 3, or 5) cells. Two weeks after peritoneal inoculation, mice bearing established A1847 tumors are given PsV (IV, IP or IT) followed two days later with CAR T cells injected IV. Mice are sacrificed when they became distressed or moribund and the tumor mass is quantified, preferentially by imaging (e.g., of luciferase-expressing tumor cells). In all experiments, blood is collected throughout the duration to measure CAR T cell proliferation and expansion, and to assess cytokine secretion. Subsets of the animals are humanely euthanized at various time points to measure tumor infiltration and tumor viability.

Another example of a syngeneic tumor model is TC1, tumor cells derived from primary murine lung cells transformed with oncogenes E6, E7 and mutant Ha-ras (Lin 1996). When subcutaneously implanted tumors reach 40-60 mm$^3$ in size, $10^7$-$10^{10}$ infectious units of tumor antigen expressing PsV is administered intravenously or intratumorally. Two days later, transduced and expanded antigen-specific CAR T cells ($10^5$-$10^9$), or placenta-derived multipotent cells (PDMCs), are injected, e.g., via intravenous, intraperitoneal and intratumoral routes. Tumor growth is specifically inhibited by CAR T-cells because they specifically interact with the tumor's surface expressed foreign antigen (e.g., CD19 delivered by PsV). Epitope spreading can also be measured in the TC-1 model by measuring T-cell responses to endogenous tumor specific proteins (HPV16 E6 and E7) in order to determine if anti-tumor immunity is generated.

REFERENCES

Brentjens R J, Santos E, Nikhamin Y, Yeh R, Matsushita M, La Perle K, Quintás-Cardama A, Larson S M, Sadelain M. Genetically targeted T cells eradicate systemic acute lymphoblastic leukemia xenografts. Clin Cancer Res. 2007 Sep. 15; 13(18 Pt 1):5426-35.

Buck C B, Thompson C D. Production of papillomavirus-based gene transfer vectors. Curr Protoc Cell Biol. 2007 December; Chapter 26:Unit 26.1.

Davila M L, Kloss C C, Gunset G, Sadelain M. CD19 CAR-targeted T cells induce long-term remission and B Cell Aplasia in an immunocompetent mouse model of B cell acute lymphoblastic leukemia. PLoS One. 2013 Apr. 9; 8(4):e61338.

Gallardo H F, Tan C, Ory D, Sadelain M. Recombinant retroviruses pseudotyped with the vesicular stomatitis virus G glycoprotein mediate both stable gene transfer and pseudotransduction in human peripheral blood lymphocytes. Blood. 1997 Aug. 1; 90(3):952-7.

Lee J, Sadelain M, Brentjens R. Retroviral transduction of murine primary T lymphocytes. Methods Mol Biol. 2009; 506:83-96.

Lin K Y, Guarnieri F G, Staveley-O'Canoll K F, Levitsky H I, August J T, Pardoll D M, Wu T C. Treatment of established tumors with a novel vaccine that enhances major histocompatibility class II presentation of tumor antigen. Cancer Res. 1996 Jan. 1; 56(1):21-6.

Salmon P, Trono D. Production and titration of lentiviral vectors. Curr Protoc Hum Genet. 2007 July; Chapter 12:Unit 12.10.

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A method comprising
   (i) delivering to a tumor of a subject an engineered nucleic acid encoding an antigen, wherein the engineered nucleic acid is delivered via a tumor-selective vehicle or via intratumoral injection, wherein the tumor expresses the antigen and
   (ii) administering to the subject an immune cell expressing a chimeric receptor that binds to the antigen; wherein the antigen comprises an epitope of CD19, CD20, CD21, CD22, CD45, BCMA, HER2 (ErbB2), EGFRvIII, B7-H3, B7-H6, FAP, FRa, EpCAM, GD2, ROR1, PSMA, or IL13Ralpha2, wherein the immune cell binds to the expressed antigen, thereby resulting in killing of the tumor.

2. The method of claim 1, wherein the tumor antigen is or comprises an epitope of CD19.

3. The method of claim 2, wherein the tumor antigen is selected from full length CD19, a fragment of CD19, or a linear epitope of CD19.

4. The method of claim 1, wherein the engineered nucleic acid encoding the antigen is encapsulated within the tumor-selective vehicle.

5. The method of claim 1, wherein tumor-selective vehicle is a virus or a pseudovirus.

6. The method of claim 5, wherein the tumor-selective vehicle is an oncolytic virus, a chimeric virus, a virus that is modified to target tumor cells, a papillomavirus, or a pseudovirus.

7. The method of claim 6, wherein the tumor-selective vehicle is an oncolytic virus selected from an adenovirus, a vaccinia virus, a Sindbis virus, a Seneca valley virus, a Coxsackie virus, a measles virus, a reovirus, a vaccinia virus, a Newcastle disease virus, a vesicular stomatitis virus, a herpes simplex virus, a poliovirus, and a parvovirus.

8. The method of claim 6, wherein the tumor-selective vehicle is a chimeric virus obtained from engineering adeno-associated viruses and bacteriophages that display tumor selective peptides.

9. The method of claim 6, wherein the tumor-selective vehicle is an adeno-associated virus (AAV) that is modified to target tumor cells.

10. The method of claim 6, wherein the tumor-selective vehicle is a human papillomavirus, a modified human papillomavirus, a non-human papillomavirus, or a modified non-human papillomavirus.

11. The method of claim 1, wherein tumor-selective vehicle is or comprises a natural polymer, a synthetic polymer, a cationic peptide, a cell-penetrating peptide, a biodegradable nanoparticle, a liposome, a lipoplex, a polyplex, a micelle, a dendrimer, a gel, a mucoadhesive or a silicon nanoneedle.

12. The method of claim 1, wherein the tumor-selective vehicle comprises a tumor-targeting agent.

13. The method of claim 1, wherein the engineered nucleic acid encoding an antigen is a deoxyribonucleic acid (DNA) or a ribonucleic acid (RNA).

14. The method of claim 13, wherein the engineered nucleic acid encoding an antigen is a messenger RNA (mRNA).

15. The method of claim 1, wherein the immune cell is leukocyte.

16. The method of claim 1, wherein the immune cell is a T cell, a B cell, an NK cell, an NKT cell, or a dendritic cell.

17. The method of claim 1, wherein the tumor-selective vehicle is delivered via a parenteral, enteric or topical route, or wherein the engineered nucleic acid is injected into the tumor.

* * * * *